(12) United States Patent
Sato et al.

(10) Patent No.: US 6,653,110 B2
(45) Date of Patent: Nov. 25, 2003

(54) METHOD FOR PRODUCING L-GLUTAMIC ACID

(75) Inventors: Masakazu Sato, Kawasaki (JP); Naoki Akiyoshi, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 10/077,751

(22) Filed: Feb. 20, 2002

(65) Prior Publication Data

US 2002/0192772 A1 Dec. 19, 2002

(30) Foreign Application Priority Data

Feb. 20, 2001 (JP) ........................................ 2001-044135

(51) Int. Cl.$^7$ ................................................ C12P 13/04
(52) U.S. Cl. ....................................................... 435/110
(58) Field of Search ......................................... 435/110

(56) References Cited

U.S. PATENT DOCUMENTS

| 3,032,474 | A | | 5/1962 | Foster et al. | |
| 3,220,929 | A | | 11/1965 | Kinoshita et al. | |
| 5,908,768 | A | | 6/1999 | Ono et al. | |
| 6,331,419 | B1 | * | 12/2001 | Moriya et al. | ............... 435/110 |
| 2001/0019836 | A1 | | 9/2001 | Hisao et al. | |

FOREIGN PATENT DOCUMENTS

| EP | 0 636 695 | 2/1995 |
| EP | 0 670 370 | 9/1995 |
| EP | 0 952 221 | 10/1999 |
| EP | 0 999 282 | 5/2000 |
| EP | 1 078 989 | 2/2001 |
| JP | 62000288 | 1/1987 |
| WO | WO 97/08294 | 3/1997 |

OTHER PUBLICATIONS

"Recent Advances in the Physiology and Genetics of Amino Acid–Producing Bacteria", Abstract of Crit. Rev. Biotechnol., 1995, vol. 15, No. 1, pp. 73–103.

J. Zaldivar, et al., "Effect of Organic Acids on the Growth and Fermentation of Ethanologenic *Escherichia coli* LY01", Biotechnology and Bioengineering, 1999, vol. 66, No. 4, pp. 203–210.

Ueda: "Some fundamental problems of continuous L–glutamic acid fermentation" Fermentation Advances. Symposium, 1969, pp. 43–62, xp002107644 *the whole document*.

Abstract of Crit Rev Biotechnol, 1995, vol. 15, No. 1, pp. 73–103 "Recent Advances in the Physiology and Genetics of Amino Acid–Producing Bacteria".

Kwei–Chao Chao et al., A Glutamic Acid–Producing Bacillus$^1$, vol. 77, pp. 715–725, Nov. 10, 1958.

R.M. Borichewski, "Keto Acids as Growth–limiting Factors in Autotrophic Growth of Thiobacillus Thiooxidans", Journal of Bacteriology, Feb., 1967, pp. 597–599.

* cited by examiner

Primary Examiner—Herbert J. Lilling
(74) Attorney, Agent, or Firm—Oblon, Spivak, McClelland, Maier & Neustadt, P.C.

(57) ABSTRACT

A method for producing L-glutamic acid by fermentation, which comprises culturing a microorganism having L-glutamic acid-producing ability in a medium having pH of 5.0 or less, wherein a total content of an organic acid that inhibits growth of the microorganism at the pH is one at which the growth of the microorganism is not inhibited; and a method for producing L-glutamic acid by fermentation, which comprises culturing a microorganism having L-glutamic acid-producing ability at a first pH at which growth of the microorganism is not inhibited by an organic acid in a medium, and then culturing the microorganism at a second pH that is suitable for L-glutamic acid production by the microorganism and is lower than the first pH.

15 Claims, 11 Drawing Sheets

[88.0% / 935 aa]

```
  1' MQNSAMKPWLDSSWLAGANQSYIEQLYEDFLTDPDSVDAVWRSMFQQLPGTGVKPEQFHS
     ***** * ****** * ***** ******************* *** ************ ****
  1" MQNSALKAWLDSSYLSGANQSWIEQLYEDFLTDPDSVDANWRSTFQQLPGTGVKPDQFHS

61' ATREYFRRLAKDASRYTSSVTDPATNSKQVKVLQLINAFRFRGHQEANLDPLGLWKQDRV
     .************ *   ** ** ************* ****** ********** ** *
 61" QTREYFRRLAKDASRYSSTISDPDTNVKQVKVLQLINAYRFRGHQHANLDPLGLWQQDKV

121' ADLDPAFHDLTDADFQESFNVGSFAIGKETMKLADLFDALKQTYCGSIGAEYMHINNTEE
     ***** ***** ***** ******* ******** * ********** ********* ***
121" ADLDPSFHDLTEADFQETFNVGSFASGKETMKLGELLEALKQTYCGPIGAEYMHITSTEE

181' KRWIQQRIESGASQTSFSGEEKKGFLKELTAAEGLEKYLGAKFPGAKRFSLEGGDALVPM
     **********   *  **** ** *********** ********************** **
181" KRWIQQRIESG--RATFNSEEKKRFLSELTAAEGLERYLGAKFPGAKRFSLEGGDALIPM

241' LREMIRHAGKSGTREVVLGMAHRGRLNVLINVLGKKPQDLFDEFSGKHKEHLGTGDVKYH
     * ******** ****************** *************** ****************
239" LKEMIRHAGNSGTREVVLGMAHRGRLNVLVNVLGKKPQDLFDEFAGKHKEHLGTGDVKYH

301' MGFSSDIETEGGLVHLALAFNPSHLEIVSPVVMGSVRARLDRLAEPVSNKVLPITIHGDA
     ******* * ******************** ********** ** ************
299" MGFSSDFQTDGGLVHLALAFNPSHLEIVSPVVIGSVRARLDRLDEPSSNKVLPITIHGDA

361' AVIGQGVVQETLNMSQARGYEVGGTVRIVINNQVGFTTSNPKDARSTPYCTDIGKMVLAP
     ** ************ ***************************  *************** **
359" AVTGQGVVQETLNMSKARGYEVGGTVRIVINNQVGFTTSNPLDARSTPYCTDIGKMVQAP

421' IFHVNADDPEAVAFVTRLALDYRNTFKRDVFIDLVCYRRHGHNEADEPSATQPLMYQKIK
     ********************* ************** *********************
419" IFHVNADDPEAVAFVTRLALDFRNTFKRDVFIDLVSYRRHGHNEADEPSATQPLMYQKIK

481' KHPTPRKIYADRLEGEGVASQEDATEMVNLYRDALDAGECVVPEWRPMSLHSFTWSPYLN
     *********** ** * ** ******************* *****  ************
479" KHPTPRKIYADKLEQEKVATLEDATEMVNLYRDALDAGDCVVAEWRPMNMHSFTWSPYLN

541' HEWDEPYPAQVDMKRLKELALRISQVPEQIEVQSRVAKIYNDRKLMAEGEKAFDWGGAEN
     ***** ** * ***** *** *** *** **** ********** ** **** ********
539" HEWDEEYPNKVEMKRLQELAKRISTVPEAVEMQSRVAKIYGDRQAMAAGEKLFDWGGAEN

601' LAYATLVDEGIPVRLSGEDSGRGTFFHRHAVVHNQANGSTYTPLHHIHNSQGEFKVWDSV
     **********************************  *** ********** ** * ******
599" LAYATLVDEGIPVRLSGEDSGRGTFFHRHAVIHNQSNGSTYTPLQHIHNGQGAFRVWDSV

661' LSEEAVLAFEYGYATAEPRVLTIWEAQFGDFANGAQVVIDQFISSGEQKWGRMCGLVMLL
     ********************** *************************************
659" LSEEAVLAFEYGYATAEPRTLTIWEAQFGDFANGAQVVIDQFISSGEQKWGRMCGLVMLL

721' PHGYEGQGPEHSSARLERYLQLCAEQNMQVCVPSTPAQVYHMLRRQALRGMRRPLVVMSP
     ************************************************************
719" PHGYEGQGPEHSSARLERYLQLCAEQNMQVCVPSTPAQVYHMLRRQALRGMRRPLVVMSP

781' KSLLRHPLAISSLDELANGSFQPAIGEIDDLDPQGVKRVVLCSGKVYYDLLEQRRKDEKT
     *********** *** ***** * ******* *** ****** ****************
779" KSLLRHPLAVSSLEELANGTFLPAIGEIDELDPKGVKRVVMCSGKVYYDLLEQRRKNNQH

841' DVAIVRIEQLYPFPHQAVQEALKAYSHVQDFVWCQEEPLNQGAWYCSQHHFRDVVPFGAT
     ************** *  **  ** ***************************** ****
839" DVAIVRIEQLYPFPHKAMQEVLQQFAHVKDFVWCQEEPLNQGAWYCSQHHFREVIPFGAS

901' LRYAGRPASASPAVGYMSVHQQQQQDLVNDALNVN
     **************************  ************
899" LRYAGRPASASPAVGYMSVHQKQQQDLVNDALNVE
```

```
  1' MSSVDILVPDLPESVADATVATWHKKPGDAVSRDEVIVEIETDKVVLEVPASADGVLEAV
     ************************************ **** ******************* * **
  1" MSSVDILVPDLPESVADATVATWHKKPGDAVVRDEVLVEIETDKVVLEVPASADGILDAV

61' LEDEGATVTSRQILGRLKEGNSAGKESSAKAESNDTTPAQRQTASLEEESSDALSPAIRR
     **** * ************ ******** *** * ****** ***** *** *********
 61" LEDEGTTVTSRQILGRLREGNSAGKETSAKSEEKASTPAQRQQASLEEQNNDALSPAIRR

121' LIAEHNLDAAQIKGTGVGGRLTREDVEKHLANKPQAEKAAAPAAGAATAQQPVANRSEKR
     * ******** ********************* * * **** * ** *** * ******
121" LLAEHNLDASAIKGTGVGGRLTREDVEKHLAKAPAKE--SAPAAAAPAAQPALAARSEKR

181' VPMTRLRKRVAERLLEAKNSTAMLTTFNEINMKPIMDLRKQYGDAFEKRHGVRLGFMSFY
     ********************************* ***************** ****** *********
179" VPMTRLRKRVAERLLEAKNSTAMLTTFNEVNMKPIMDLRKQYGEAFEKRHGIRLGFMSFY

241' IKAVVEALKRYPEVNASIDGEDVVYHNYFDVSIAVSTPRGLVTPVLRDVDALSMADIEKK
     ********************** **************** ***************** * ********
239" VKAVVEALKRYPEVNASIDGDDVVYHNYFDVSMAVSTPRGLVTPVLRDVDTLGMADIEKK

301' IKELAVKGRDGKLTVDDLTGGNFTITNGGVFGSLMSTPIINPPQSAILGMHAIKDRPMAV
     ***************** ******************************************
299" IKELAVKGRDGKLTVEDLTGGNFTITNGGVFGSLMSTPIINPPQSAILGMHAIKDRPMAV

361' NGQVVILPMMYLALSYDHRLIDGRESVGYLVAVKEMLEDPARLLLDV
     **** ************************** ** ** **** ******
359" NGQVEILPMMYLALSYDHRLIDGRESVGFLVTIKELLEDPTRLLLDV
```

```
  1' MNLHEYQAKQLFARYGMPAPTGYACTTPREAEEAASKIGAG
     ******************** *************************
  1" MNLHEYQAKQLFARYGLPAPVGYACTTPREAEEAASKIGAGPWVVKCQVHAGGRGKAGGV
```

```
  1'                                         AFSVFRCHSIMNCVSVCPKGLNPTRAIGHIKSMLLQRSA
                                             ************************************** *
181" FLIDSRDTETDSRLDGLSDAFSVFRCHSIMNCVSVCPKGLNPTRAIGHIKSMLLQRNA
```

FIG. 5

SEQUENCE LISTING

<160> NUMBER OF SEQ ID NOS: 8

<210> SEQ ID NO 1
<211> LENGTH: 935
<212> TYPE: PRT
<213> ORGANISM: Enterobacter agglomerans

<400> SEQUENCE: 1

```
Met Gln Asn Ser Ala Met Lys Pro Trp Leu Asp Ser Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60
```

-continued

```
Tyr Phe Arg Arg Leu Ala Lys Asp Ala Ser Arg Tyr Thr Ser Ser Val
 65                  70                  75                  80

Thr Asp Pro Ala Thr Asn Ser Lys Gln Val Lys Val Leu Gln Leu Ile
                 85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175

Asn Thr Glu Glu Lys Arg Trp Ile Gln Gln Arg Ile Glu Ser Gly Ala
            180                 185                 190

Ser Gln Thr Ser Phe Ser Gly Glu Glu Lys Lys Gly Phe Leu Lys Glu
        195                 200                 205

Leu Thr Ala Ala Glu Gly Leu Glu Lys Tyr Leu Gly Ala Lys Phe Pro
    210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
        275                 280                 285

Lys Glu His Leu Gly Thr Gly Asp Val Lys Tyr His Met Gly Phe Ser
    290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Ile Gly Gln Gly Val Val
        355                 360                 365

Gln Glu Thr Leu Asn Met Ser Gln Ala Arg Gly Tyr Glu Val Gly Gly
    370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
        435                 440                 445

Asp Val Phe Ile Asp Leu Val Cys Tyr Arg Arg His Gly His Asn Glu
    450                 455                 460

Ala Asp Glu Pro Ser Ala Thr Gln Pro Leu Met Tyr Gln Lys Ile Lys
465                 470                 475                 480
```

-continued

```
Lys His Pro Thr Pro Arg Lys Ile Tyr Ala Asp Arg Leu Glu Gly Glu
                485                 490                 495
Gly Val Ala Ser Gln Glu Asp Ala Thr Glu Met Val Asn Leu Tyr Arg
            500                 505                 510
Asp Ala Leu Asp Ala Gly Glu Cys Val Val Pro Glu Trp Arg Pro Met
            515                 520                 525
Ser Leu His Ser Phe Thr Trp Ser Pro Tyr Leu Asn His Glu Trp Asp
    530                 535                 540
Glu Pro Tyr Pro Ala Gln Val Asp Met Lys Arg Leu Lys Glu Leu Ala
545                 550                 555                 560
Leu Arg Ile Ser Gln Val Pro Glu Gln Ile Glu Val Gln Ser Arg Val
                565                 570                 575
Ala Lys Ile Tyr Asn Asp Arg Lys Leu Met Ala Glu Gly Glu Lys Ala
                580                 585                 590
Phe Asp Trp Gly Gly Ala Glu Asn Leu Ala Tyr Ala Thr Leu Val Asp
            595                 600                 605
Glu Gly Ile Pro Val Arg Leu Ser Gly Glu Asp Ser Gly Arg Gly Thr
            610                 615                 620
Phe Phe His Arg His Ala Val Val His Asn Gln Ala Asn Gly Ser Thr
625                 630                 635                 640
Tyr Thr Pro Leu His His Ile His Asn Ser Gln Gly Glu Phe Lys Val
                645                 650                 655
Trp Asp Ser Val Leu Ser Glu Glu Ala Val Leu Ala Phe Glu Tyr Gly
            660                 665                 670
Tyr Ala Thr Ala Glu Pro Arg Val Leu Thr Ile Trp Glu Ala Gln Phe
            675                 680                 685
Gly Asp Phe Ala Asn Gly Ala Gln Val Val Ile Asp Gln Phe Ile Ser
    690                 695                 700
Ser Gly Glu Gln Lys Trp Gly Arg Met Cys Gly Leu Val Met Leu Leu
705                 710                 715                 720
Pro His Gly Tyr Glu Gly Gln Gly Pro Glu His Ser Ser Ala Arg Leu
                725                 730                 735
Glu Arg Tyr Leu Gln Leu Cys Ala Glu Gln Asn Met Gln Val Cys Val
                740                 745                 750
Pro Ser Thr Pro Ala Gln Val Tyr His Met Leu Arg Arg Gln Ala Leu
            755                 760                 765
Arg Gly Met Arg Arg Pro Leu Val Val Met Ser Pro Lys Ser Leu Leu
770                 775                 780
Arg His Pro Leu Ala Ile Ser Ser Leu Asp Glu Leu Ala Asn Gly Ser
785                 790                 795                 800
Phe Gln Pro Ala Ile Gly Glu Ile Asp Asp Leu Asp Pro Gln Gly Val
                805                 810                 815
Lys Arg Val Val Leu Cys Ser Gly Lys Val Tyr Tyr Asp Leu Leu Glu
                820                 825                 830
Gln Arg Arg Lys Asp Glu Lys Thr Asp Val Ala Ile Val Arg Ile Glu
            835                 840                 845
Gln Leu Tyr Pro Phe Pro His Gln Ala Val Gln Glu Ala Leu Lys Ala
    850                 855                 860
Tyr Ser His Val Gln Asp Phe Val Trp Cys Gln Glu Glu Pro Leu Asn
865                 870                 875                 880
Gln Gly Ala Trp Tyr Cys Ser Gln His His Phe Arg Asp Val Val Pro
                885                 890                 895
Phe Gly Ala Thr Leu Arg Tyr Ala Gly Arg Pro Ala Ser Ala Ser Pro
```

```
                  900               905               910
Ala Val Gly Tyr Met Ser Val His Gln Gln Gln Gln Asp Leu Val
        915               920               925

Asn Asp Ala Leu Asn Val Asn
        930             935

<210> SEQ ID NO 2
<211> LENGTH: 407
<212> TYPE: PRT
<213> ORGANISM: Enterobacter agglomerans

<400> SEQUENCE: 2

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Ser
                20                  25                  30

Arg Asp Glu Val Ile Val Glu Ile Glu Thr Asp Lys Val Val Leu Glu
            35                  40                  45

Val Pro Ala Ser Ala Asp Gly Val Leu Glu Ala Val Leu Glu Asp Glu
        50                  55                  60

Gly Ala Thr Val Thr Ser Arg Gln Ile Leu Gly Arg Leu Lys Glu Gly
65                  70                  75                  80

Asn Ser Ala Gly Lys Glu Ser Ser Ala Lys Ala Glu Ser Asn Asp Thr
                85                  90                  95

Thr Pro Ala Gln Arg Gln Thr Ala Ser Leu Glu Glu Ser Ser Asp
            100                 105                 110

Ala Leu Ser Pro Ala Ile Arg Arg Leu Ile Ala Glu His Asn Leu Asp
        115                 120                 125

Ala Ala Gln Ile Lys Gly Thr Gly Val Gly Gly Arg Leu Thr Arg Glu
    130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
    210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Ile Lys Glu Leu
    290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
                325                 330                 335
```

-continued

```
Thr Pro Ile Ile Asn Pro Pro Gln Ser Ala Ile Leu Gly Met His Ala
                340                 345                 350

Ile Lys Asp Arg Pro Met Ala Val Asn Gly Gln Val Val Ile Leu Pro
            355                 360                 365

Met Met Tyr Leu Ala Leu Ser Tyr Asp His Arg Leu Ile Asp Gly Arg
        370                 375                 380

Glu Ser Val Gly Tyr Leu Val Ala Val Lys Glu Met Leu Glu Asp Pro
385                 390                 395                 400

Ala Arg Leu Leu Leu Asp Val
                405

<210> SEQ ID NO 3
<211> LENGTH: 41
<212> TYPE: PRT
<213> ORGANISM: Enterobacter agglomerans

<400> SEQUENCE: 3

Met Asn Leu His Glu Tyr Gln Ala Lys Gln Leu Phe Ala Arg Tyr Gly
1               5                   10                  15

Met Pro Ala Pro Thr Gly Tyr Ala Cys Thr Thr Pro Arg Glu Ala Glu
            20                  25                  30

Glu Ala Ala Ser Lys Ile Gly Ala Gly
        35                  40

<210> SEQ ID NO 4
<211> LENGTH: 39
<212> TYPE: PRT
<213> ORGANISM: Enterobacter agglomerans

<400> SEQUENCE: 4

Ala Phe Ser Val Phe Arg Cys His Ser Ile Met Asn Cys Val Ser Val
1               5                   10                  15

Cys Pro Lys Gly Leu Asn Pro Thr Arg Ala Ile Gly His Ile Lys Ser
            20                  25                  30

Met Leu Leu Gln Arg Ser Ala
        35

<210> SEQ ID NO 5
<211> LENGTH: 933
<212> TYPE: PRT
<213> ORGANISM: Escherichia coli

<400> SEQUENCE: 5

Met Gln Asn Ser Ala Leu Lys Ala Trp Leu Asp Ser Ser Tyr Leu Ser
1               5                   10                  15

Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu
        35                  40                  45

Pro Gly Thr Gly Val Lys Pro Asp Gln Phe His Ser Gln Thr Arg Glu
    50                  55                  60

Tyr Phe Arg Arg Leu Ala Lys Asp Ala Ser Arg Tyr Ser Ser Thr Ile
65                  70                  75                  80

Ser Asp Pro Asp Thr Asn Val Lys Gln Val Lys Val Leu Gln Leu Ile
                85                  90                  95

Asn Ala Tyr Arg Phe Arg Gly His Gln His Ala Asn Leu Asp Pro Leu
            100                 105                 110

Gly Leu Trp Gln Gln Asp Lys Val Ala Asp Leu Asp Pro Ser Phe His
```

-continued

```
            115                 120                 125
Asp Leu Thr Glu Ala Asp Phe Gln Glu Thr Phe Asn Val Gly Ser Phe
    130                 135                 140
Ala Ser Gly Lys Glu Thr Met Lys Leu Gly Leu Leu Glu Ala Leu
145                 150                 155                 160
Lys Gln Thr Tyr Cys Gly Pro Ile Gly Ala Glu Tyr Met His Ile Thr
                165                 170                 175
Ser Thr Glu Glu Lys Arg Trp Ile Gln Gln Arg Ile Glu Ser Gly Arg
            180                 185                 190
Ala Thr Phe Asn Ser Glu Glu Lys Arg Phe Leu Ser Glu Leu Thr
            195                 200                 205
Ala Ala Glu Gly Leu Glu Arg Tyr Leu Gly Ala Lys Phe Pro Gly Ala
    210                 215                 220
Lys Arg Phe Ser Leu Glu Gly Asp Ala Leu Ile Pro Met Leu Lys
225                 230                 235                 240
Glu Met Ile Arg His Ala Gly Asn Ser Gly Thr Arg Glu Val Val Leu
                245                 250                 255
Gly Met Ala His Arg Gly Arg Leu Asn Val Leu Val Asn Val Leu Gly
            260                 265                 270
Lys Lys Pro Gln Asp Leu Phe Asp Glu Phe Ala Gly Lys His Lys Glu
            275                 280                 285
His Leu Gly Thr Gly Asp Val Lys Tyr His Met Gly Phe Ser Ser Asp
    290                 295                 300
Phe Gln Thr Asp Gly Gly Leu Val His Leu Ala Leu Ala Phe Asn Pro
305                 310                 315                 320
Ser His Leu Glu Ile Val Ser Pro Val Val Ile Gly Ser Val Arg Ala
                325                 330                 335
Arg Leu Asp Arg Leu Asp Glu Pro Ser Ser Asn Lys Val Leu Pro Ile
            340                 345                 350
Thr Ile His Gly Asp Ala Ala Val Thr Gly Gln Gly Val Val Gln Glu
            355                 360                 365
Thr Leu Asn Met Ser Lys Ala Arg Gly Tyr Glu Val Gly Gly Thr Val
    370                 375                 380
Arg Ile Val Ile Asn Asn Gln Val Gly Phe Thr Thr Ser Asn Pro Leu
385                 390                 395                 400
Asp Ala Arg Ser Thr Pro Tyr Cys Thr Asp Ile Gly Lys Met Val Gln
                405                 410                 415
Ala Pro Ile Phe His Val Asn Ala Asp Asp Pro Glu Ala Val Ala Phe
            420                 425                 430
Val Thr Arg Leu Ala Leu Asp Phe Arg Asn Thr Phe Lys Arg Asp Val
            435                 440                 445
Phe Ile Asp Leu Val Ser Tyr Arg Arg His Gly His Asn Glu Ala Asp
    450                 455                 460
Glu Pro Ser Ala Thr Gln Pro Leu Met Tyr Gln Lys Ile Lys Lys His
465                 470                 475                 480
Pro Thr Pro Arg Lys Ile Tyr Ala Asp Lys Leu Glu Gln Glu Lys Val
                485                 490                 495
Ala Thr Leu Glu Asp Ala Thr Glu Met Val Asn Leu Tyr Arg Asp Ala
            500                 505                 510
Leu Asp Ala Gly Asp Cys Val Val Ala Glu Trp Arg Pro Met Asn Met
            515                 520                 525
His Ser Phe Thr Trp Ser Pro Tyr Leu Asn His Glu Trp Asp Glu Glu
    530                 535                 540
```

-continued

```
Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
            565                 570                 575

Ile Tyr Gly Asp Arg Gln Ala Met Ala Ala Gly Glu Lys Leu Phe Asp
        580                 585                 590

Trp Gly Gly Ala Glu Asn Leu Ala Tyr Ala Thr Leu Val Asp Glu Gly
    595                 600                 605

Ile Pro Val Arg Leu Ser Gly Glu Asp Ser Gly Arg Gly Thr Phe Phe
610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
        675                 680                 685

Phe Ala Asn Gly Ala Gln Val Val Ile Asp Gln Phe Ile Ser Ser Gly
    690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
        755                 760                 765

Met Arg Arg Pro Leu Val Val Met Ser Pro Lys Ser Leu Leu Arg His
770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
        835                 840                 845

Tyr Pro Phe Pro His Lys Ala Met Gln Glu Val Leu Gln Gln Phe Ala
850                 855                 860

His Val Lys Asp Phe Val Trp Cys Gln Glu Glu Pro Leu Asn Gln Gly
865                 870                 875                 880

Ala Trp Tyr Cys Ser Gln His His Phe Arg Glu Val Ile Pro Phe Gly
                885                 890                 895

Ala Ser Leu Arg Tyr Ala Gly Arg Pro Ala Ser Ala Ser Pro Ala Val
            900                 905                 910

Gly Tyr Met Ser Val His Gln Lys Gln Gln Asp Leu Val Asn Asp
        915                 920                 925

Ala Leu Asn Val Glu
    930

<210> SEQ ID NO 6
<211> LENGTH: 405
```

```
<212> TYPE: PRT
<213> ORGANISM: Escherichia coli

<400> SEQUENCE: 6

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Val
            20                  25                  30

Arg Asp Glu Val Leu Val Glu Ile Glu Thr Asp Lys Val Val Leu Glu
        35                  40                  45

Val Pro Ala Ser Ala Asp Gly Ile Leu Asp Ala Val Leu Glu Asp Glu
    50                  55                  60

Gly Thr Thr Val Thr Ser Arg Gln Ile Leu Gly Arg Leu Arg Glu Gly
65                  70                  75                  80

Asn Ser Ala Gly Lys Glu Thr Ser Ala Lys Ser Glu Glu Lys Ala Ser
                85                  90                  95

Thr Pro Ala Gln Arg Gln Gln Ala Ser Leu Glu Glu Gln Asn Asn Asp
            100                 105                 110

Ala Leu Ser Pro Ala Ile Arg Arg Leu Leu Ala Glu His Asn Leu Asp
        115                 120                 125

Ala Ser Ala Ile Lys Gly Thr Gly Val Gly Gly Arg Leu Thr Arg Glu
    130                 135                 140

Asp Val Glu Lys His Leu Ala Lys Ala Pro Ala Lys Glu Ser Ala Pro
145                 150                 155                 160

Ala Ala Ala Ala Pro Ala Ala Gln Pro Ala Leu Ala Ala Arg Ser Glu
                165                 170                 175

Lys Arg Val Pro Met Thr Arg Leu Arg Lys Arg Val Ala Glu Arg Leu
            180                 185                 190

Leu Glu Ala Lys Asn Ser Thr Ala Met Leu Thr Thr Phe Asn Glu Val
        195                 200                 205

Asn Met Lys Pro Ile Met Asp Leu Arg Lys Gln Tyr Gly Glu Ala Phe
    210                 215                 220

Glu Lys Arg His Gly Ile Arg Leu Gly Phe Met Ser Phe Tyr Val Lys
225                 230                 235                 240

Ala Val Val Glu Ala Leu Lys Arg Tyr Pro Glu Val Asn Ala Ser Ile
                245                 250                 255

Asp Gly Asp Asp Val Val Tyr His Asn Tyr Phe Asp Val Ser Met Ala
            260                 265                 270

Val Ser Thr Pro Arg Gly Leu Val Thr Pro Val Leu Arg Asp Val Asp
        275                 280                 285

Thr Leu Gly Met Ala Asp Ile Glu Lys Lys Ile Lys Glu Leu Ala Val
    290                 295                 300

Lys Gly Arg Asp Gly Lys Leu Thr Val Glu Asp Leu Thr Gly Gly Asn
305                 310                 315                 320

Phe Thr Ile Thr Asn Gly Gly Val Phe Gly Ser Leu Met Ser Thr Pro
                325                 330                 335

Ile Ile Asn Pro Pro Gln Ser Ala Ile Leu Gly Met His Ala Ile Lys
            340                 345                 350

Asp Arg Pro Met Ala Val Asn Gly Gln Val Glu Ile Leu Pro Met Met
        355                 360                 365

Tyr Leu Ala Leu Ser Tyr Asp His Arg Leu Ile Asp Gly Arg Glu Ser
    370                 375                 380

Val Gly Phe Leu Val Thr Ile Lys Glu Leu Leu Glu Asp Pro Thr Arg
385                 390                 395                 400
```

```
Leu Leu Leu Asp Val
            405

<210> SEQ ID NO 7
<211> LENGTH: 60
<212> TYPE: PRT
<213> ORGANISM: Escherichia coli

<400> SEQUENCE: 7

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
            20                  25                  30

Glu Ala Ala Ser Lys Ile Gly Ala Gly Pro Trp Val Val Lys Cys Gln
        35                  40                  45

Val His Ala Gly Gly Arg Gly Lys Ala Gly Gly Val
    50                  55                  60

<210> SEQ ID NO 8
<211> LENGTH: 58
<212> TYPE: PRT
<213> ORGANISM: Escherichia coli

<400> SEQUENCE: 8

Phe Leu Ile Asp Ser Arg Asp Thr Glu Thr Asp Ser Arg Leu Asp Gly
1               5                   10                  15

Leu Ser Asp Ala Phe Ser Val Phe Arg Cys His Ser Ile Met Asn Cys
            20                  25                  30

Val Ser Val Cys Pro Lys Gly Leu Asn Pro Thr Arg Ala Ile Gly His
        35                  40                  45

Ile Lys Ser Met Leu Leu Gln Arg Asn Ala
    50                  55
```

METHOD FOR PRODUCING L-GLUTAMIC ACID

BACKGROUND OF THE INVENTION

The present invention relates to a method for producing L-glutamic acid by fermentation. L-Glutamic acid is widely used as a raw material of seasonings and so forth.

L-Glutamic acid is produced mainly by fermentation utilizing so-called L-glutamic acid-producing coryneform bacteria belonging to the genus Brevibacterium, Corynebacterium or Microbacterium or mutant strains thereof (Amino Acid Fermentation, Gakkai Shuppan Center, pp.195–215, 1986). As methods for producing L-glutamic acid by fermentation by using other bacterial strains, there are known a method using a microorganism belonging to the genus Bacillus, Streptomyces, Penicillium or the like (U.S. Pat. No. 3,220,929), a method using a microorganism belonging to the genus Pseudomonas, Arthrobacter, Serratia, Candida or the like (U.S. Pat. No. 3,563,857), a method using a microorganism belonging to the genus Bacillus, Pseudomonas, Serratia, *Aerobacter aerogenes* (currently referred to as *Enterobacter aerogenes*) or the like (Japanese Patent Publication (Kokoku) No. 32-9393), a method using a mutant strain of *Escherichia coli* (Japanese Patent Application Laid-open (Kokai) No. 5-244970) and so forth. In addition, the inventors of the present invention proposed a method for producing L-glutamic acid by using a microorganism belonging to the genus Klebsiella, Erwinia or Pantoea (Japanese Patent Application Laid-open No. 2000-106869).

Further, there have been disclosed various techniques for improving L-glutamic acid-producing ability by enhancing activities of L-glutamic acid biosynthetic enzymes through use of recombinant DNA techniques. For example, it was reported that introduction of a gene coding for citrate synthase derived from *Escherichia coli* or *Corynebacterium glutamicum* was effective for enhancement of L-glutamic acid-producing ability in Corynebacterium or Brevibacterium bacteria (Japanese Patent Publication (Kokoku) No. 7-121228). In addition, Japanese Patent Application Laid-open No. 61-268185 discloses a cell harboring recombinant DNA containing a glutamate dehydrogenase gene derived from Corynebacterium bacteria. Further, Japanese Patent Application Laid-open No. 63-214189 discloses a technique for increasing L-glutamic acid-producing ability by amplifying a glutamate dehydrogenase gene, an isocitrate dehydrogenase gene, an aconitate hydratase gene and a citrate synthase gene.

Although L-glutamic acid productivity has been considerably increased by the aforementioned breeding of microorganisms or improvement of production methods, development of methods for more efficiently producing L-glutamic acid at a lower cost is required to meet to further increase of the demand in future.

There is known a method wherein fermentation is performed as L-amino acid accumulated in culture is crystallized (Japanese Patent Application Laid-open No. 62-288). In this method, the L-amino acid concentration in the culture is maintained below a certain level by precipitating the accumulated L-amino acid in the culture. Specifically, L-tryptophan, L-tyrosine or L-leucine is precipitated during fermentation by adjusting temperature and pH of the culture or adding a surfactant to a medium.

While a method of carrying out fermentation with precipitation of L-amino acid accompanied is known as described above, amino acids suitable for this method are those showing a relatively low water solubility, and no example of applying the method to highly water-soluble amino acids such as L-glutamic acid is known. In addition, the medium must have low pH to precipitate L-glutamic acid. However, L-glutamic acid-producing bacteria such as those mentioned above cannot grow under an acidic condition, and therefore L-glutamic acid fermentation is performed under neutral conditions (U.S. Pat. Nos. 3,220,929 and 3,032,474; K. C. Chao & J. W. Foster, J. Bacteriol., 77, pp.715–725 (1959)). Thus, production of L-glutamic acid by fermentation accompanied by precipitation is not known. Furthermore, it is known that growth of most acidophile bacteria is inhibited by organic acids such as acetic acid, lactic acid and succinic acid (Yasuro Oshima Ed., "Extreme Environment Microorganism Handbook", p.231, Science Forum; R. M. Borichewski, J. Bacteriol., 93, pp.597–599 (1967) etc.). Therefore, it is considered that many microorganisms are susceptible to L-glutamic acid, which is also an organic acid, under acidic conditions, and there has been no report that search of microorganisms showing L-glutamic acid-producing ability under acidic conditions was attempted.

SUMMARY OF THE INVENTION

An object of the present invention is to provide a method for producing L-glutamic acid by fermentation, which enables efficient L-glutamic acid production even when a material containing an organic acid that inhibits growth of a microorganism at a low pH, is used as a sugar source.

The inventors of the present invention found that, at a neutral pH, an L-glutamic acid-producing bacterium consumed an organic acid that inhibited growth of the L-glutamic acid-producing bacterium at a low pH, and that based on this property, L-glutamic acid could be efficiently produced by using a material containing an organic acid that inhibited growth of a microorganism at a low pH as a sugar source. Thus, they accomplished the present invention.

The present invention provides the followings.

(1) A method for producing L-glutamic acid by fermentation, which comprises culturing a microorganism having L-glutamic acid-producing ability in a medium having pH of 5.0 or less, wherein a total content of an organic acid that inhibits growth of the microorganism at the pH is one at which the growth of the microorganism is not inhibited.

(2) The method according to (1), wherein L-glutamic acid is produced and accumulated in the medium with precipitation of the L-glutamic acid accompanied, during the culture in the medium.

(3) The method according to (1) or (2), wherein the total content of the organic acid is 0.4 g/L or less.

(4) The method according to any one of (1) to (3), wherein the organic acid is an organic acid having carbon number of 1 to 3.

(5) The method according to any one of (1) to (4), wherein the microorganism belongs to the genus Enterobacter.

(6) The method according to (5), wherein the microorganism is Enterobacter agglomerans.

(7) The method according to any one of (1) to (6), wherein the microorganism can metabolize a carbon source in a liquid medium containing L-glutamic acid at a saturation concentration and the carbon source, at a specific pH, and has an ability to accumulate L-glutamic acid in an amount exceeding the saturation concentration of L-glutamic acid in the liquid medium at the pH.

(8) The method according to (7), wherein the specific pH is 5.0 or less.

(9) A method for producing L-glutamic acid by fermentation, which comprises culturing a microorganism having L-glutamic acid-producing ability at a first pH at which growth of the microorganism is not inhibited by an organic acid in a medium, and then culturing the microorganism at a second pH that is suitable for L-glutamic acid production by the microorganism and is lower than the first pH.
(10) The method according to (9), wherein the organic acid is an organic acid having carbon number of 1 to 3.
(11) The method according to (9) or (10), wherein the second pH is 3.0 to 5.0.
(12) The method according to any one of (9) to (11), wherein the culture at the first pH is performed while pH of the medium is maintained to be the first pH by adding an alkalizing substance to the medium.
(13) The method according to (12), which comprising lowering pH of the medium by controlling the addition amount of the alkalizing substance after the culture at the first pH.
(14) The method according to any one of (9) to (13), wherein the culture at the first pH is continued until the organic acid in the medium is depleted.
(15) The method according to any one of (9) to (14), wherein the microorganism belongs to the genus Enterobacter.
(16) The method according to (15), wherein the microorganism is *Enterobacter agglomerans*.
(17) The method according to any one of (9) to (16), wherein the microorganism can metabolize a carbon source in a liquid medium containing L-glutamic acid at a saturation concentration and the carbon source, at a specific pH, and has an ability to accumulate L-glutamic acid in an amount exceeding the saturation concentration of L-glutamic acid in the liquid medium at the pH.
(18) The method according to (17), wherein the specific pH is 5.0 or less.
(19) The method according to (17) or (18), wherein the pH suitable for the L-glutamic acid production is a pH at which L-glutamic acid produced by the microorganism precipitates in the medium, and L-glutamic acid is produced and accumulated with precipitation of the L-glutamic acid accompanied, during the culture in the medium at that pH.

According to the methods of the present invention, L-glutamic acid can be efficiently produced even when a material containing an organic acid that inhibits growth of a microorganism, such as blackstrap molasses, is used as a sugar source.

BRIEF EXPLANATION OF THE DRAWINGS

FIG. 2 shows comparison of an amino acid sequence deduced from a nucleotide sequence of an sucA gene derived from *Enterobacter agglomerans* and that derived from *Eseherichia coli* (upper: *Enterobacter agglomerans* (SEQ ID NO: 1), column: *Eseherichia coli* (SEQ ID NO: 5), the same shall apply to the followings).

FIG. 3 shows comparison of an amino acid sequence deduced from a nucleotide sequence of an sucB gene derived from *Enterobacter agglomerans* (SEQ ID NO 2) and that derived from *Escherichia coli* (SEQ ID NO: 6).

FIG. 4 shows comparison of an amino acid sequence deduced from a nucleotide sequence of an sucC gene derived from *Enterobacter agglomerans* (SEQ ID NO 3) and that derived from *Escherichia coli* (SEQ ID NO 7).

FIG. 5 shows comparison of an amino acid sequence deduced from a nucleotide sequence of an sdhB gene derived from *Enterobacter agglomerans* (SEQ ID NO 4), and that derived from *Escherichia coli* (SEQ ID NO 8).

DETAILED DESCRIPTION OF THE INVENTION

Figure 1:
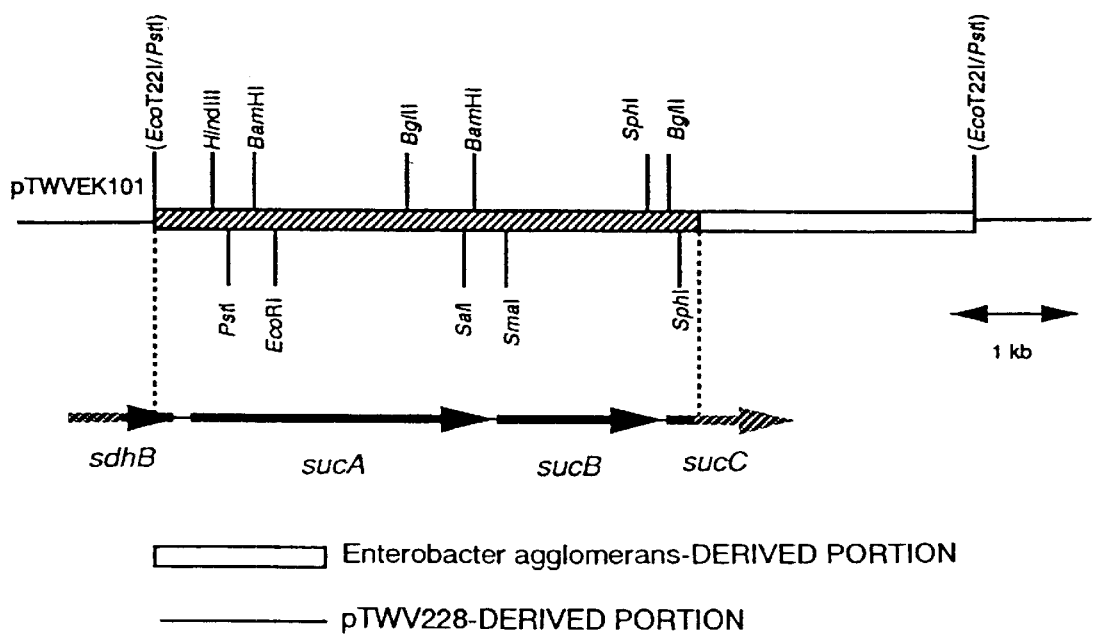
FIG. 1 is a restriction enzyme map of a DNA fragment derived from *Enterobacter agglomerans* in pTWVEK101.

Hereafter, the present invention will be explained in detail.

The production method according to the first embodiment of the present invention (henceforth also referred to as the "first production method of the present invention") is a method for producing L-glutamic acid by fermentation, which comprises culturing a microorganism having L-glutamic acid-producing ability (henceforth also referred to as "L-glutamic acid-producing bacterium") in a medium having pH of 5.0 or less, wherein a total content of an organic acid that inhibits growth of the microorganism at the pH is one at which growth of the microorganism is not inhibited.

In the first production method of the present invention, it is preferred that L-glutamic acid is produced and accumulated by culture in a medium with precipitation of the L-glutamic acid accompanied. This can be attained by adjusting pH of the medium to a pH at which the produced L-glutamic acid precipitates. Such a pH is usually 3.0 to 5.0. It is considered that, in the production of L-glutamic acid by fermentation, the reduction of the productivity by L-glutamic acid accumulated in the medium at a high concentration constitutes an obstacle to improvement of the productivity. For example, a microbial cell has a discharge system and an uptake system for L-glutamic acid, and if L-glutamic acid once discharged into the medium is taken up into the cell again, not only the production efficiency is reduced, but also it results in inhibition of the reactions for the L-glutamic acid biosynthesis. By performing the culture at a pH at which the produced L-glutamic acid precipitates, such reduction of productivity due to the accumulation of L-glutamic acid at a high concentration can be obviated.

The medium has a pH of preferably 4.5 or less, more preferably 4.0 or less.

In this embodiment, the organic acid that inhibits growth of a microorganism at pH of medium means an organic acid that has an inhibitory effect on inhibition of growth of the microorganism when it exists at a certain concentration (usually 0.5 g/L or more) in the medium at the pH, and it is usually an organic acid having carbon number of 1 to 3, i.e., formic acid, acetic acid or propionic acid.

The total content of the organic acid is preferably 0.4 g/L or less, more preferably 0.3 g/L or less, further preferably 0.2 g/L or less.

The production method according to the second embodiment of the present invention (henceforth also referred to as "the second production method of the present invention") is a method for producing L-glutamic acid by fermentation, which comprises culturing a microorganism having L-glutamic acid-producing ability at a first pH at which growth of the microorganism is not inhibited by an organic acid in a medium, and then culturing the microorganism at a second pH that is suitable for L-glutamic acid production by the microorganism and is lower than the first pH.

It was found that an L-glutamic acid-producing bacterium generally suffered from inhibition of growth by an organic acid under an acid condition, whereas it could consume an organic acid under a neutral condition. Based on this property, by effecting cell growth at a neutral pH and then changing pH into acidic pH to produce L-glutamic acid, it becomes possible to obtain higher productivity and it also becomes possible to use various materials as a sugar source.

In this embodiment, the organic acid means an organic acid that has an inhibitory effect on growth of microorganism when it exists at a certain concentration (usually 0.5 g/L or more) in a medium at the second pH, and it is usually an organic acid having carbon number of 1 to 3, i.e., formic acid, acetic acid or propionic acid.

The first pH and the second pH are selected so that they should meet the properties of an L-glutamic acid-producing bacterium to be used. These pH values can be easily measured by those skilled in the art. For example, the pH at which inhibition of growth of microorganism is not caused by an organic acid in a medium can be determined by culturing an L-glutamic acid-producing bacterium in media containing an organic acid adjusted to various pH values, measuring cell amounts based on absorbance or the like, and comparing the cell amounts with cell amounts of the L-glutamic acid-producing bacterium cultured under the same conditions except that the media do not contain the organic acid. The pH suitable for the production of L-glutamic acid refers to pH at which L-glutamic acid is accumulated in a medium, determinable by culturing an L-glutamic acid-producing bacterium in media of various pH values. Specifically, it can be determined by measuring amounts of L-glutamic acid accumulated in media of various pH values and comparing them.

The first pH is not particularly limited so long as growth of microorganism is not inhibited by the organic acid in the medium, but it is usually 5.0 to 8.0.

The second pH is preferably a pH at which the produced L-glutamic acid precipitates, and such pH is usually 3.0 to 5.0. As explained for the first production method of the present invention, the reduction of productivity by accumulation of L-glutamic acid at a high concentration can be obviated by performing the culture at the pH at which the produced L-glutamic acid precipitates.

The first pH and the second pH may not be strictly constant during the culture so long as the advantage of the present invention can be obtained, and they may fluctuate.

The L-glutamic acid-producing bacterium produces L-glutamic acid even at the first pH, and therefore pH is lowered by the produced L-glutamic acid. Therefore, the culture at the first pH is preferably performed while maintaining pH of the medium at the first pH by adding an alkalizing substance to the medium.

Although the alkalizing substance is not particularly limited so long as it does not adversely affect the growth of the L-glutamic acid-producing bacterium or L-glutamic acid production, ammonia gas is preferred.

The pH of the medium may be lowered from the first pH to the second pH by adding an acidic substance. However, pH is lowered by L-glutamic acid produced by the L-glutamic acid-producing bacterium during the culture as described above. Therefore, it is preferable to lower the pH of the medium from the first pH to the second pH by controlling the addition amount of the alkalizing substance, because the addition of the acidic substance can be omitted.

The culture at the first pH may be continued until the organic acid in the medium is depleted. The depletion means that the amount of the organic acid decreases to a level at which growth of the L-glutamic acid-producing bacterium is not inhibited during the culture at the second pH. Such a level of the organic acid can be easily measured by those skilled in the art. For example, the level can be determined by culturing an L-glutamic acid-producing bacterium in media containing an organic acid at various concentrations at the second pH, measuring cell amounts of the L-glutamic acid-producing bacterium, and comparing the cell amounts with cell amounts of the L-glutamic acid-producing bacterium cultured under the same conditions except that the media do not contain the organic acid. Generally, as the second pH becomes lower, the level of the organic acid also becomes lower.

The L-glutamic acid-producing bacterium used in the first production method of the present invention and the second production method of the present invention is a microorganism that accumulates a significant amount of L-glutamic acid in a medium when it is cultured in the medium. Examples thereof include microorganisms belonging to the genus Enterobacter. Preferred is *Enterobacter agglomerans*.

Further, the L-glutamic acid-producing bacterium used in the first and second production methods of the present invention is preferably a microorganism that can metabolize a carbon source in a liquid medium containing L-glutamic acid at a saturation concentration and the carbon source, at a specific pH, and has an ability to accumulate L-glutamic acid in an amount exceeding the saturation concentration of L-glutamic acid in the liquid medium at the aforementioned pH (henceforth also referred to as "L-glutamic acid-accumulating microorganism"). The aforementioned specific pH is preferably a pH at which L-glutamic acid precipitates in the medium, and such a pH is usually 5.0 or less.

The "saturation concentration" means a concentration of L-glutamic acid dissolved in the liquid medium when the liquid medium is saturated with L-glutamic acid.

When an L-glutamic acid-accumulating microorganism is used, the pH suitable for the production of L-glutamic acid is preferably a pH at which L-glutamic acid precipitates in the medium. By performing the culture at this pH, L-glutamic is produced and accumulated in the medium with its precipitation accompanied.

The L-glutamic acid-accumulating microorganism can be obtained as follows. A sample containing microorganisms is inoculated into a liquid medium containing L-glutamic acid at a saturation concentration and a carbon source, at a specific pH, and a strain that metabolizes the carbon source is selected. Although the specific pH is not particularly limited, it is usually about 5.0 or less, preferably about 4.5 or less, further preferably about 4.3 or less. The L-glutamic acid-accumulating microorganism is used for production of L-glutamic acid by fermentation with precipitation of the L-glutamic acid accompanied. If the pH is too high, it becomes difficult to allow the microorganism to produce L-glutamic acid in an amount sufficient for precipitation. Therefore, pH is preferably in the aforementioned range.

If pH of an aqueous solution containing L-glutamic acid is lowered, the solubility of L-glutamic acid significantly falls around pKa of γ-carboxyl group (4.25, 25° C.). The solubility becomes the lowest at the isoelectric point (pH 3.2) and L-glutamic acid exceeding the amount corresponding to the saturation concentration is precipitated. While it depends on the medium composition, L-glutamic acid is dissolved in an amount of 10–20 g/L at pH 3.2, 30–40 g/L at pH 4.0 and 50–60 g/L at pH 4.7, at about 30° C. Usually pH does not need to be made 3.0 or lower, because the L-glutamic acid precipitating effect reaches its upper limit when pH goes below a certain value. However, pH may be 3.0 or less.

In addition, the expression that a microorganism "can metabolize a carbon source" means that it can proliferate or can consume a carbon source even though it cannot proliferate, that is, it indicates that it catabolizes a carbon source such as sugars or organic acids. Specifically, for example, if a microorganism proliferates when it is cultured in a liquid medium containing L-glutamic acid at a saturation concentration at pH 5.0 to 4.0, preferably pH 4.5 to 4.0, more preferably pH 4.3 to 4.0, particularly preferably pH 4.0, at an appropriate temperature, for example, 28° C., 37° C. or 50° C., for 2 to 4 days, this microorganism can metabolize the carbon source in the medium. Further, for example, if a microorganism consume a carbon source even though the microorganism does not proliferate, when it is cultured in a synthetic liquid medium containing L-glutamic acid at a saturation concentration at pH 5.0 to 4.0, preferably pH 4.5 to 4.0, more preferably pH 4.3 to 4.0, particularly preferably pH 4.0, at an appropriate temperature, for example, 28° C., 37° C. or 50° C., for 2 to 4 days, the microorganism is a microorganism that can metabolize the carbon source in the medium.

The microorganism that can metabolize a carbon source include a microorganism that can grow in the aforementioned liquid medium.

Further, the expression that a microorganism "can grow" means that it can proliferate or can produce L-glutamic acid even though it cannot proliferate. Specifically, for example, if a microorganism proliferates when it is cultured in a liquid medium containing L-glutamic acid at a saturation concentration at pH 5.0 to 4.0, preferably pH 4.5 to 4.0, more preferably pH 4.3 to 4.0, particularly preferably pH 4.0, at an appropriate temperature, for example, 28° C., 37° C. or 50° C., for 2 to 4 days, this microorganism can grow in the medium. Further, for example, if a microorganism increases an amount of L-glutamic acid in a synthetic liquid medium even though the microorganism does not proliferate, when the microorganism is cultured in the synthetic liquid medium containing L-glutamic acid at a saturation concentration at pH 5.0 to 4.0, preferably pH 4.5 to 4.0, more preferably pH 4.3 to 4.0, particularly preferably pH 4.0, at an appropriate temperature, for example, 28° C., 37° C. or 50° C., for 2 to 4 days, this microorganism is a microorganism that can grow in the medium.

The selection described above may be repeated two or more times under the same conditions or with changing pH or the concentration of L-glutamic acid. A selection for an early stage can be performed in a medium containing L-glutamic acid at a concentration lower than the saturation concentration, and thereafter a subsequent selection can be performed in a medium containing L-glutamic acid at a saturation concentration. Further, strains with favorable properties such as superior proliferation rate may be selected.

The L-glutamic acid-accumulating microorganism is a microorganism that has an ability to accumulate L-glutamic acid in an amount exceeding the amount corresponding to the saturation concentration of L-glutamic acid in a liquid medium, in addition to the properties described above. The pH of the aforementioned liquid medium is preferably the same as or close to that of the medium used for screening a microorganism having the aforementioned properties. Usually, a microorganism becomes susceptible to L-glutamic acid at a high concentration as pH becomes lower. Therefore, it is preferred that pH is not low in view of resistance to L-glutamic acid, but low pH is preferred in view of production of L-glutamic acid with its precipitation accompanied. To satisfy these conditions, pH can be in the range of 3 to 5, preferably 4 to 5, more preferably 4 to 4.7, further preferably 4 to 4.5, particularly preferably 4.0 to 4.3.

As the L-glutamic acid-accumulating microorganism of or breeding materials therefor, there can be mentioned, for example, microorganisms belonging to the genus Enterobacter, Klebsiella, Serratia, Pantoea, Erwinia, Escherichia, Corynebacterium, Alicyclobacillus, Bacillus, Saccharomyces or the like. Among these, microorganisms belonging to the genus Enterobacter are preferred. Hereafter, the microorganism of the present invention will be explained mainly for microorganisms belonging to the genus Enterobacter. However, the microorganism is not limited to those belonging to the genus Enterobacter, and those belonging to other genera can be similarly used.

As a microorganism belonging to the Enterobacter, there can be specifically mentioned *Enterobacter agglomerans*, preferably the *Enterobacter agglomerans* AJ13355 strain. This strain was isolated from soil in Iwata-shi, Shizuoka, Japan as a strain that can proliferate in a medium containing L-glutamic acid and a carbon source at low pH.

The physiological properties of AJ13355 are shown below:

(1) Gram staining: negative
(2) Behavior against oxygen: facultative anaerobic
(3) Catalase: positive
(4) Oxidase: negative
(5) Nitrate-reducing ability: negative
(6) Voges-Proskauer test: positive
(7) Methyl Red test: negative
(8) Urease: negative
(9) Indole production: positive
(10) Motility: motile
(11) $H_2S$ production in TSI medium: weakly active
(12) β-Galactosidase: positive
(13) Saccharide-assimilating property:
    Arabinose: positive
    Sucrose: positive
    Lactose: positive
    xylose: positive
    Sorbitol: positive
    Inositol: positive
    Trehalose: positive
    Maltose: positive
    Glucose: positive
    Adonitol: negative Raffinose: positive
Salicin: negative
Melibiose: positive
(14) Glycerose-assimilating property: positive
(15) Organic acid-assimilating property:
  Citric acid: positive
  Tartaric acid: negative
  Gluconic acid: positive
  Acetic acid: positive
  Malonic acid: negative
(16) Arginine dehydratase: negative
(17) Ornithine decarboxylase: negative
(18) Lysine decarboxylase: negative
(19) Phenylalanine deaminase: negative
(20) Pigment formation: yellow
(21) Gelatin liquefaction ability: positive
(22) Growth pH: growth possible at pH 4, good growth at pH 4.5 to 7
(23) Growth temperature: good growth at 25° C., good growth at 30° C., good growth at 37° C., growth possible at 42° C., growth impossible at 45° C.

Based on these bacteriological properties, AJ13355 was determined as *Enterobacter agglomerans*.

The *Enterobacter agglomerans* AJ 13355 was deposited at the National Institute of Bioscience and Human-Technology, Agency of Industrial Science and Technology, Ministry of International Trade and Industry (now, International Patent Organism Depositary, National Institute of Advanced Industrial Science and Technology, AIST Tsukuba Central 6, 1-1, Higashi 1-chome, Tsukuba-shi, Ibaraki-Ken 305-8566, Japan) on Feb. 19, 1998 and received an accession number of FERM P-16644. It as then transferred to an international deposition at that depository under the provisions of Budapest Treaty of Jan. 11, 1999 and received an accession number of FERM BP-6614.

The L-glutamic acid-accumulating microorganism may be a microorganism originally having L-glutamic acid-producing ability or one having L-glutamic acid-producing ability imparted or enhanced by breeding through use of mutagenesis treatment, recombinant DNA techniques or the like.

The L-glutamic acid-producing ability can be imparted or enhanced by, for example, increasing activity of an enzyme that catalyzes a reaction for biosynthesis of L-glutamic acid. The L-glutamic acid-producing ability can also be enhanced by decreasing or eliminating activity of an enzyme that catalyzes a reaction which branches off from the biosynthetic pathway of L-glutamic acid and generates a compound other than L-glutamic acid.

As examples of the enzyme that catalyzes the reaction for biosynthesis of L-glutamic acid, there can be mentioned glutamate dehydrogenase (hereafter, also referred to as "GDH"), glutamine synthetase, glutamate synthase, isocitrate dehydrogenase, aconitate hydratase, citrate synthase (hereafter, also referred to as "CS"), phosphoenolpyruvate carboxylase (hereafter, also referred to as "PEPC"), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and so forth. Among these enzymes, one, two or three of CS, PEPC and GDH are preferred. Further, it is preferred that the activities of all the three enzymes, CS, PEPC and GDH, are enhanced in the L-glutamic acid-accumulating microorganism. In particular, CS of *Brevibacterium lactofermentum* is preferred, because it does not suffer from inhibition by α-ketoglutaric acid, L-glutamic acid and NADH.

In order to enhance the activity of CS, PEPC or GDH, for example, a gene coding for CS, PEPC or GDH can be cloned on an appropriate plasmid and a host microorganism can be transformed with the obtained plasmid. The copy number of the gene coding for CS, PEPC or GDH (hereafter, abbreviated as "gltA gene", "ppc gene" and "gdhA gene", respectively) in the transformed strain cell increases, resulting in the increase of the activity of CS, PEPC or GDH.

The cloned gltA, ppc and gdhA genes are introduced into the aforementioned starting parent strain solely or in combination of arbitrary two or three kinds of them. When two or three kinds of the genes are introduced, two or three kinds of the genes may be cloned on one kind of plasmid and introduced into the host, or separately cloned on two or three kinds of plasmids that can coexist and introduced into the host.

Two or more kinds of genes coding for an enzyme of the same kind, but derived from different microorganisms, may be introduced into the same host.

The plasmids described above are not particularly limited so long as they are autonomously replicable in a cell of a microorganism belonging to, for example, the genus Enterobacter or the like. However, there can be mentioned, for example, pUC19, pUC18, pBR322, pHSG299, pHSG298, pHSG399, pHSG398, RSF1010, pMW119, pMW118, pMW219, pMW218, pACYC177, pACYC184 and so forth. Besides these, vectors of phage DNA can also be used.

Transformation can be performed by, for example, the method of D. M. Morrison (Methods in Enzymology, 68, 326 (1979)), the method wherein permeability of recipient bacterium cells for DNA is increased by treating the cells with calcium chloride (Mandel M. and Higa A., J. Mol. Biol., 53, 159 (1970)), electroporation (Miller J. H., "A Short Course in Bacterial Genetics", Cold Spring Harbor Laboratory Press, U.S.A., 1992) or the like.

The activity of CS, PEPC or GDH can also be increased by allowing multiple copies of the gltA gene, the ppc gene or the gdhA gene to be present on chromosomal DNA of the aforementioned starting parent strain to be a host. In order to introduce multiple copies of the gltA gene, the ppc gene or the gdhA gene on chromosomal DNA of a microorganism belonging to the genus Enterobacter or the like, a sequence of which multiple copies are present on the chromosomal DNA, such as repetitive DNA and inverted repeats present at terminus of a transposable element, can be used. Alternatively, multiple copies of the genes can be introduced onto chromosomal DNA by utilizing transfer of a transposon containing the gltA gene, the ppc gene or the gdhA gene. As a result, the copy number of gltA gene, the ppc gene or the gdhA gene in a transformed strain cell is increased, and thus the activity of CS, PEPC or GDH is increased.

As organisms used as a source of the gltA gene, the ppc gene or the gdhA gene of which copy number is to be increased, any organism can be used so long as it has activity of CS, PEPC or GDH. Inter alia, bacteria, which are prokaryotes, for example, those belonging to the genus Enterobacter, Klebsiella, Erwinia, Pantoea, Serratia, Escherichia, Corynebacterium, Brevibacterium or Bacillus are preferred. As specific examples, there can be mentioned *Escherichia coli, Brevibacterium lactofermentum* and so forth. The gltA gene, the ppc gene and the gdhA gene can be obtained from chromosomal DNA of the microorganisms described above.

The gltA gene, the ppc gene and the gdhA gene can be obtained by using a mutant strain which is deficient in the activity of CS, PEPC or GDH to isolate a DNA fragment that supplements its auxotrophy from chromosomal DNA of the aforementioned microorganism. Further, since the nucleotide sequences of these genes of Escherichia and Corynebacterium bacteria have already been elucidated (Biochemistry, 22, pp.5243–5249, (1983); J. Biochem., 95, pp.909–916, (1984); Gene, 27, pp.193–199, (1984); Microbiology, 140, pp.1817–1828, (1994); Mol. Gen. Genet., 218, pp.330–339, (1989); Molecular Microbiology, 6, pp.317–326, (1992)), they can also be obtained by PCR utilizing primers synthesized based on each nucleotide sequence and chromosomal DNA as a template.

The activity of CS, PEPC or GDH can also be increased by enhancing the expression of the gltA gene, the ppc gene or the gdhA gene, besides the aforementioned amplification of the genes. For example, the expression can be enhanced by replacing a promoter for the gltA gene, the ppc gene or the gdhA gene with another stronger promoter. For example, lac promoter, trp promoter, trc promoter, tac promoter, $P_R$ promoter and $P_L$ promoter of the lamda phage and so forth are known as strong promoters. The gltA gene, the ppc gene and the gdhA gene of which promoter is replaced are cloned on a plasmid and introduced into the host microorganism, or introduced onto the chromosomal DNA of the host microorganism by using repetitive DNA, inverted repeat, transposon or the like.

The activity of CS, PEPC or GDH can also be increased by replacing the promoter of the gltA gene, the ppc gene or the gdhA gene on the chromosome with another stronger promoter (see WO87/03006 and Japanese Patent Application Laid-open No. 61-268183), or inserting a strong promoter in the upstream of the coding sequence of each gene (see Gene, 29, pp.231–241 (1984)). Specifically, homologous recombination can be performed between the gltA gene, the ppc gene or the gdhA gene of which promoter is replaced with a stronger one or DNA containing a part thereof and the corresponding gene on the chromosome.

Examples of the enzyme that catalyzes the reaction which branches off from the biosynthetic pathway of the L-glutamic acid and generates a compound other than L-glutamic acid include α-ketoglutarate dehydrogenase (hereafter, also referred to as "αKGDH"), isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase and so forth. Among these enzymes, αKGDH is preferred.

In order to decrease or eliminate the activities of the aforementioned enzymes in a microorganism belonging to the genus Enterobacter or the like, mutations for decreasing or eliminating the intracellular activity of the enzymes can be introduced into genes of the aforementioned enzymes by a usual mutagenesis treatment method or a genetic engineering method.

Examples of the mutagenesis treatment method include, for example, methods utilizing irradiation with X-ray or ultraviolet ray, methods utilizing treatment with a mutagenesis agent such as N-methyl-N'-nitro-N-nitrosoguanidine, and so forth. The site of a gene where the mutation is introduced may be in a coding region coding for an enzyme protein or a region for regulating expression such as a promoter.

Examples of the genetic engineering methods include, for example, methods utilizing gene recombination, transduction, cell fusion and so forth. For example, a drug resistance gene is inserted into a cloned target gene to prepare a gene that has lost its function (defective gene).

Subsequently, this defective gene is introduced into a cell of a host microorganism, and the target gene on the chromosome is replaced with the aforementioned defective gene by utilizing homologous recombination (gene disruption).

Decrease or deficiency of intracellular activity of the target enzyme and the degree of decrease of the activity c an be confirmed by measuring the enzyme activity of a cell extract or a purified fraction thereof obtained from a candidate strain and comparing it with that of a wild strain. For example, the αKGDH activity can be measured by the method of Reed et al. (Reed L. J. and Mukherjee B. B., Methods in Enzymology, 13, pp.55–61 (1969)).

Depending on the target enzyme, a target mutant strain can be selected based on a phenotype of the mutant strain. For example, a mutant strain wherein the αKGDH activity is eliminated or decreased cannot proliferate or shows a markedly reduced proliferation rate in a minimal medium containing glucose or a minimal medium containing acetic acid or L-glutamic acid as an exclusive carbon source under an aerobic culture condition. However, normal proliferation is enabled even under the same condition by adding succinic acid or lysine, methionine and diaminopimelic acid to a minimal medium containing glucose. By utilizing these phenomena as indicators, a mutant strain with decreased αKGDH activity or deficient in the activity can be selected.

A method for preparing an αKGDH gene-deficient strain of *Brevibacterium lactofermentum* by utilizing homologous recombination is described in detail in WO95/34672. Similar methods can be applied to other microorganisms.

Further, techniques such as cloning of genes and digestion and ligation of DNA, transformation and so forth are described in detail in Molecular Cloning, 2nd Edition, Cold Spring Harbor Press (1989) and so forth.

As a specific example of a mutant strain deficient in αKGDH activity or with decreased αKGDH activity obtained as described above, there can be mentioned *Enterobacter agglomerans* AJ13356. *Enterobacter agglomerans* AJ13356 was deposited at the National Institute of Bioscience and Human-Technology, Agency of Industrial Science and Technology, Ministry of International Trade and Industry (now, International Patent Organism Depositary, National Institute of Advanced Industrial Science and Technology) on Feb. 19, 1998 and received an accession number of FERM P-16645. It was then transferred to an international deposition under the provisions of Budapest Treaty on Jan. 11, 1999 and received an accession number of FERM BP-6615. The *Enterobacter agglomerans* AJ13356 is deficient in αKGDH activity as a result of disruption of the αKGDH-E1 subunit gene (sucA).

When *Enterobacter agglomerans*, which is an example of the microorganism used in the present invention, is cultured in a medium containing a saccharide, mucus is extracellularly secreted, occasionally resulting in low operation efficiency. Therefore, when *Enterobacter agglomerans* having such a property of secreting mucus is used, it is preferable to use a mutant strain that secretes less mucus compared with a wild strain. Examples of mutagenesis treatment include, for example, methods utilizing irradiation with X-ray or ultraviolet ray, method utilizing treatment with a mutagenesis agent such as N-methyl-N'-nitro-N-nitrosoguanidine, and so forth. A mutant strain with decreased secretion of mucus can be selected by inoculating mutagenized bacterial cells in a medium containing a saccharide, for example, LB medium plate containing 5 g/L of glucose, culturing them with tilting the plate about 45 degrees and selecting a colony that does not show flowing down of mucus.

In the present invention, impartation or enhancement of L-glutamic acid-producing ability and impartation of other favorable properties such as mutation for less mucus secretion described above can be carried out in an arbitrary order.

By culturing the L-glutamic acid-accumulating microorganism in a liquid medium that is adjusted to pH condition that allows precipitation of L-glutamic acid, L-glutamic acid can be produced and accumulated with its precipitation in the medium accompanied.

The "condition that allows precipitation of L-glutamic acid produced by the microorganism" referred to herein means a condition that allows precipitation of L-glutamic acid when the L-glutamic acid-accumulating microorganism produces and accumulates L-glutamic acid. Although pH of this condition may vary depending on the L-glutamic acid-producing ability of the microorganism, it is usually 3 to 5 when the microorganism is an Enterobacter bacterium.

As the media used for culture in the first production method of the present invention, culture at the first pH and culture at the second pH in the second production method of the present invention, a usual nutrient medium containing a carbon source, a nitrogen source, mineral salts and organic trace nutrients such as amino acids and vitamins as required can be used so long as pH is adjusted so as to satisfy the predetermined condition. Either a synthetic medium or a natural medium can be used. The carbon source and the nitrogen source used in the medium can be any ones so long as they can be used by the strain to be cultured.

As the carbon source, saccharides such as glucose, glycerol, fructose, sucrose, maltose, mannose, galactose, starch hydrolysate and molasses are used. In addition, organic acids such as acetic acid and citric acid may be used each alone or in combination with another carbon source.

As the nitrogen source, ammonia, ammonium salts such as ammonium sulfate, ammonium carbonate, ammonium chloride, ammonium phosphate and ammonium acetate, nitrates and so forth are used.

As the organic trace nutrients, amino acids, vitamins, fatty acids, nucleic acids, those containing these substances such as peptone, casamino acid, yeast extract and soybean protein decomposition products are used. When an auxotrophic mutant strain that requires an amino acid and so forth for metabolization or growth is used, the required nutrient must be supplemented.

As mineral salts, phosphates, magnesium salts, calcium salts, iron salts, manganese salts and so forth are used.

As for the culture method, aeration culture at 20 to 42° C. is usually performed provided that pH is controlled to be a predetermined value.

After completion of the culture, L-glutamic acid precipitated in the culture can be collected by centrifugation, filtration or the like. L-Glutamic acid dissolved in the medium can be also collected by known methods. For example, the L-glutamic acid can be isolated by concentrating the culture broth to crystallize it or isolated by ion exchange chromatography or the like. It is also possible to crystallize L-glutamic acid dissolved in the medium and then collect the L-glutamic acid precipitated in the culture broth together with the crystallized L-glutamic acid.

In an embodiment where L-glutamic acid exceeding a saturation concentration precipitates, the concentration of L-glutamic acid dissolved in the medium is maintained at a constant level. Therefore, influence of L-glutamic acid at a high concentration on microorganisms can be reduced. Accordingly, it also becomes possible to breed a microorganism having further improved L-glutamic acid-producing ability. Further, since L-glutamic acid is precipitated as crystals, acidification of the culture broth by accumulation of L-glutamic acid is suppressed, and therefore the amount of alkali used for maintaining pH of the culture can significantly be reduced.

EXAMPLES

Hereafter, the present invention will be more specifically explained with reference to the following examples. In the examples, amino acids are L-amino acids unless otherwise indicated.

Reference Example 1
<1> Screening of Microorganism having L-glutamic Acid Resistance in Acidic Environment Screening of a microorganism having L-glutamic acid resistance in acidic environment was performed as follows. One (1) g each of about 500 samples obtained from nature including soil, fruits, plant bodies, river water and so forth was suspended in 5 mL of sterilized water, and 200 µL thereof was coated on 20 mL of solid medium adjusted to pH 4.0 with HCl. The composition of the medium was as follows: 3 g/L of glucose, 1 g/L of ammonium sulfate, 0.2 g/L of magnesium sulfate heptahydrate, 0.5 g/L of potassium dihydrogenphosphate, 0.2 g/L of sodium chloride, 0.1 g/L of calcium chloride dihydrate, 0.01 g/L of ferrous sulfate heptahydrate, 0.01 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 50 µg/L of biotin, 50 µg/L of calcium pantothenate, 50 µg/L of folic acid, 50 µg/L of inositol, 50 µg/L of niacin, 50 µg/L of p-aminobenzoic acid, 50 µg/L of pyridoxine hydrochloride, 50 µg/L of riboflavin, 50 µg/L of thiamin hydrochloride, 50 mg/L of cycloheximide and 20 g/L of agar.

The media plated with the above samples were incubated at 28° C., 37° C. or 50° C. for 2 to 4 days and 378 strains forming colonies were obtained.

Subsequently, each of the strains obtained as described above was inoculated in a test tube of 16.5 cm in length and 14 mm in diameter containing 3 mL of liquid medium (adjusted to pH 4.0 with HCl ) containing a saturation concentration of L-glutamic acid and cultured at 28° C., 37° C. or 50° C. for 24 hours to 3 days with shaking. Then, the grown strains were selected. The composition of the aforementioned medium was follows: 40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate and 2 g/L of yeast extract.

Thus, 78 strains of microorganisms showing L-glutamic acid resistance in an acidic environment were successfully obtained.

<2> Selection of Strains Showing Superior Growth Rate from Microorganisms Having L-glutamic Acid Resistance in Acidic Environment The various microorganisms having L-glutamic acid resistance in an acidic environment obtained as described above are each inoculated into a test tube of 16.5 cm in length and 14 mm in diameter containing 3 mL of medium (adjusted to pH 4.0 with HCl ) obtained by adding 20 g/L of glutamic acid and 2 g/L of glucose to M9 medium (Sambrook, J., Fritsh, E. F. and Maniatis, T., "Molecular Cloning", Cold Spring Harbor Laboratory Press, U.S.A., 1989), and the turbidity of the medium was measured in the time course to select strains showing a favorable growth rate. As a result, as a strain showing favorable growth, the AJ13355 strain was obtained from soil in Iwata-shi, Shizuoka, Japan. This strain was determined as *Enterobacter agglomerans* based on its bacteriological properties described above.

<3> Acquisition of Strain with Less Mucus Secretion from *Enterobacter Agglomerans* AJ13355 Strain Since the *Enterobacter agglomerans* AJ13355 strain extracellularly secretes mucus when cultured in a medium containing a saccharide, operation efficiency is not favorable. Therefore, a strain with less mucus secretion was obtained by the ultraviolet irradiation method (Miller, J. H. et al., "A Short Course in Bacterial Genetics; Laboratory Manual", p.150, 1992, Cold Spring Harbor Laboratory Press, U.S.A.).

The *Enterobacter agglomerans* AJ13355 strain was irradiated with ultraviolet ray for 2 minutes at a position 60 cm away from a 60-W ultraviolet lamp and cultured in LB medium overnight to fix mutation. The mutagenized strain was diluted and inoculated in LB medium containing 5 g/L of glucose and 20 g/L of agar so that about 100 colonies per plate would emerge and cultured at 30° C. overnight with tilting the plate about 45 degrees, and then 20 colonies showing not flowing down of mucus were selected.

As a strain satisfying conditions that no revertant emerged even after 5 times of subculture in LB medium containing 5 g/L of glucose and 20 g/L of agar, and that there should be observed growth equivalent to the parent strain in LB medium, LB medium containing 5 g/L of glucose and M9 medium (Sambrook, J. et al., Molecular Cloning, 2nd Edition, Cold Spring Harbor Press, U.S.A., 1989) supplemented with 20 g/L of L-glutamic acid and 2 g/L of glucose and adjusted to pH 4.5 with HCl, SC17 strain was selected from the strains selected above.

<4> Construction of Glutamic Acid-producing Bacterium from *Enterobacter Agglomerans* SC17 Strain (1) Preparation of αKGDH Deficient Strain from *Enterobacter Agglomerans* SC17 Strain A strain that was deficient in αKGDH and had enhanced L-glutamic acid biosynthetic system was prepared from the *Enterobacter Agglomerans* SC17 strain.

(i) Cloning of αKGDH Gene (Hereafter, Referred to as "sucAB") of *Enterobacter Agglomerans* AJ13355 Strain The sucAB gene of the *Enterobacter agglomerans* AJ13355 strain was cloned by selecting a DNA fragment complementing the acetic acid-unassimilating property of the αKGDH-E1 subunit gene (hereafter, referred to as "sucA")-deficient strain of *Escherichia coli* from chromosomal DNA of the *Enterobacter agglomerans* AJ13355 strain.

The chromosomal DNA of the *Enterobacter agglomerans* AJ13355 strain was isolated by a method usually employed for extracting chromosomal DNA from *Escherichia coli* (Text for Bioengineering Experiments, Edited by the Society for Bioscience and Bioengineering, Japan, pp.97–98, Baifukan, 1992). The pTWV228 (resistant to ampicillin) used as a vector was a commercial product of Takara Shuzo Co., Ltd.

The chromosomal DNA of the AJ13355 strain digested with EcoT22I and pTWV228 digested with PstI were ligated by using T4 ligase and used to transform the sucA-deficient *Escherichia coli* JRG465 strain (Herbert, J. et al., Mol. Gen. Genetics, 105, 182 (1969)). A strain growing in an acetate minimal medium was selected from the transformant strains obtained above, and a plasmid was extracted from it and designated as pTWVEK101. The *Escherichia coli* JRG465 strain harboring pTWVEK101 recovered auxotrophy for succinic acid or L-lysine and L-methionine besides the trait of acetic acid-unassimilating property. This suggests that pTWVEK101 contained the sucA gene of *Enterobacter agglomerans*.

FIG. 1 shows a restriction enzyme map of a DNA fragment derived from *Enterobacter agglomerans* in pTWVEK101. In the nucleotide sequence of the hatched portion in FIG. 1, nucleotide sequences considered to be two full length ORFs and two nucleotide sequences considered to be partial sequences of ORFs were found. As a result of homology search for these, it was revealed that the portions of which nucleotide sequences were determined contained a 3' end partial sequence of the succinate dehydrogenase iron-sulfur protein gene (sdhB), full length sucA and αKGDH-E2 subunit gene (sucB gene), and a 5' end partial sequence of the succinyl CoA synthetase β subunit gene (sucC gene). The results of comparison of the amino acid sequences deduced from these nucleotide sequences with those derived from *Escherichia coli* (Eur. J. Biochem., 141, pp.351–359 (1984); Eur. J. Biochem., 141, pp.361–374 (1984); Biochemistry, 24, pp.6245–6252 (1985)) are shown in FIGS. 2 to 5. Thus, the amino acid sequences showed very high homology to each other. In addition, it was found that a cluster of sdhB-sucA-sucB-sucC was constituted on the chromosome of *Enterobacter agglomerans* as in *Escherichia coli* (Eur. J. Biochem., 141, pp.351–359 (1984); Eur. J. Biochem., 141, pp.361–374 (1984); Biochemistry, 24, pp.6245–6252 (1985)).

(ii) Acquisition of αKGDH-deficient Strain Derived From *Enterobacter Agglomerans* SC17 Strain The homologous recombination was performed by using the sucAB gene of *Enterobacter agglomerans* obtained as described above to obtain an αKGDH-deficient strain of *Enterobacter agglomerans*.

After pTWVEK101 was digested with SphI to excise a fragment containing sucA, the fragment was blunt-ended with Klenow fragment (Takara Shuzo Co., Ltd.) and ligated with pBR322 digested with EcoRI and blunt-ended with Klenow fragment, by using T4 DNA ligase (Takara Shuzo Co., Ltd.). The obtained plasmid was digested at the restriction enzyme BglII recognition site positioned approximately at the center of sucA by using the enzyme, blunt-ended with Klenow fragment, and then ligated again by using T4 DNA ligase. It was considered that the sucA gene became unfunctional because a frameshift mutation was introduced into sucA of the plasmid newly constructed through the above procedure.

The plasmid constructed as described above was digested with a restriction enzyme ApaLI, and subjected to agarose gel electrophoresis to recover a DNA fragment containing sucA into which the frameshift mutation was introduced and a tetracycline resistance gene derived from pBR322. The recovered DNA fragment was ligated again by using T4 DNA ligase to construct a plasmid for disrupting the αKGDH gene.

The plasmid for disrupting the αKGDH gene obtained as described above was used to transform the *Enterobacter agglomerans* SC17 strain by electroporation (Miller, J. H., "A Short Course in Bacterial Genetics; Handbook", p.279, Cold Spring Harbor Laboratory Press, U.S.A., 1992), and a strain wherein sucA on the chromosome was replaced with a mutant type one of the plasmid by homologous recombination was obtained by using the tetracycline resistance as a marker. The obtained strain was designated as SC17sucA strain.

In order to confirm that the SC17sucA strain was deficient in the αKGDH activity, the enzyme activity was measured by the method of Reed et al. (Reed, L. J. and Mukherjee, B. B., Methods in Enzymology, 13, pp.55–61, (1969)) by using cells of the strain cultured in LB medium to the logarithmic growth phase. As a result, αKGDH activity of 0.073 (ΔABS/min/mg protein) was detected from the SC17 strain, whereas no αKGDH activity was detected from the SC17sucA strain, and thus it was confirmed that the sucA was eliminated as intended.

(2) Enhancement of L-glutamic Acid Biosynthesis System of *Enterobacter Agglomerans* SC17sucA Strain Subsequently, the citrate synthase gene, phosphoenolpyruvate carboxylase gene and glutamate dehydrogenase gene derived from *Escherichia coli* were introduced into the SC17sucA strain.

(i) Preparation of Plasmid Having gltA Gene, ppc Gene and gdhA Gene Derived From *Escherichia Coli*

Figure 6:
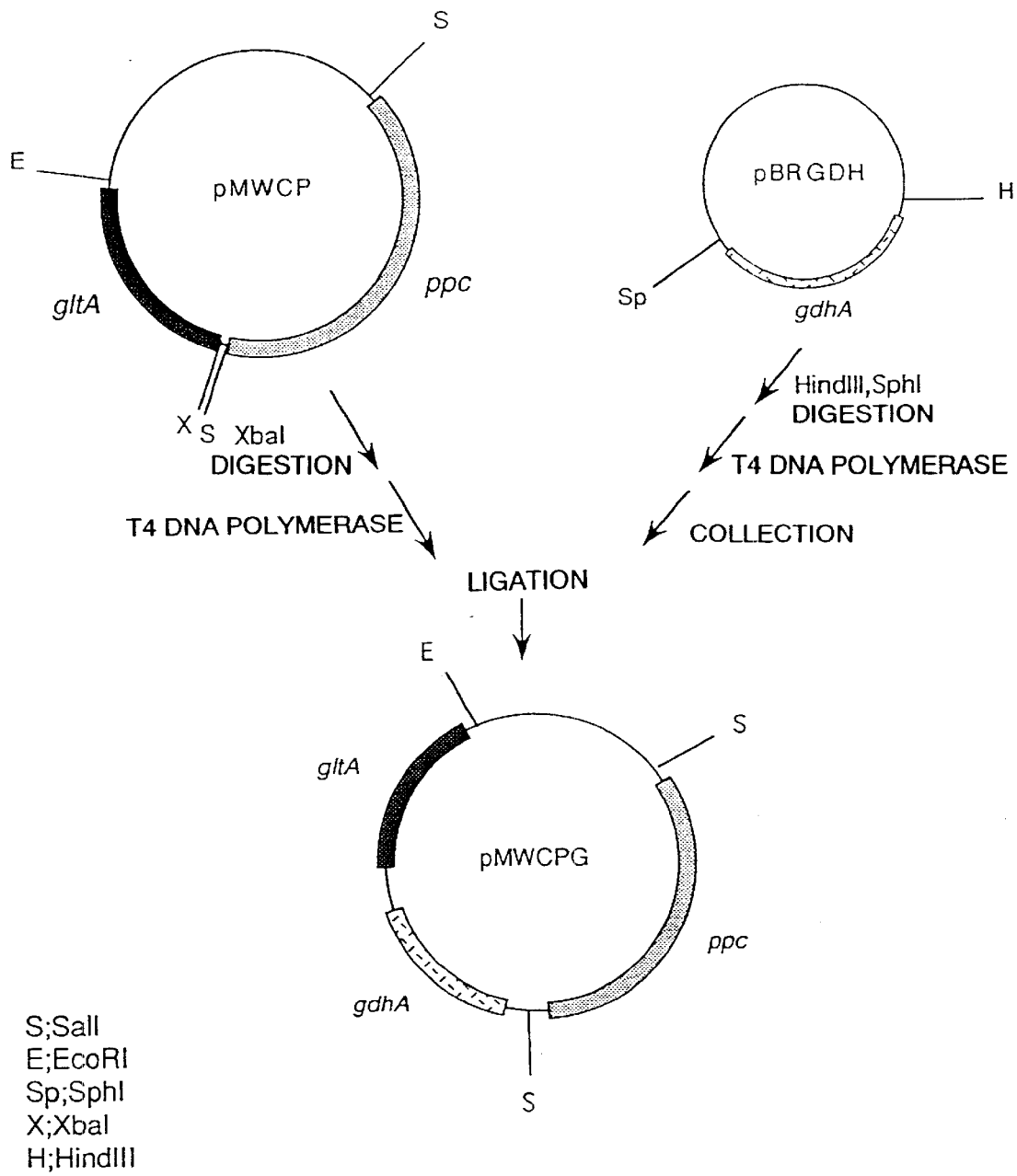
FIG. 6 shows construction of a plasmid pMWCPG containing a gltA gene, a ppc gene and a gdhA gene.
Figure 7:
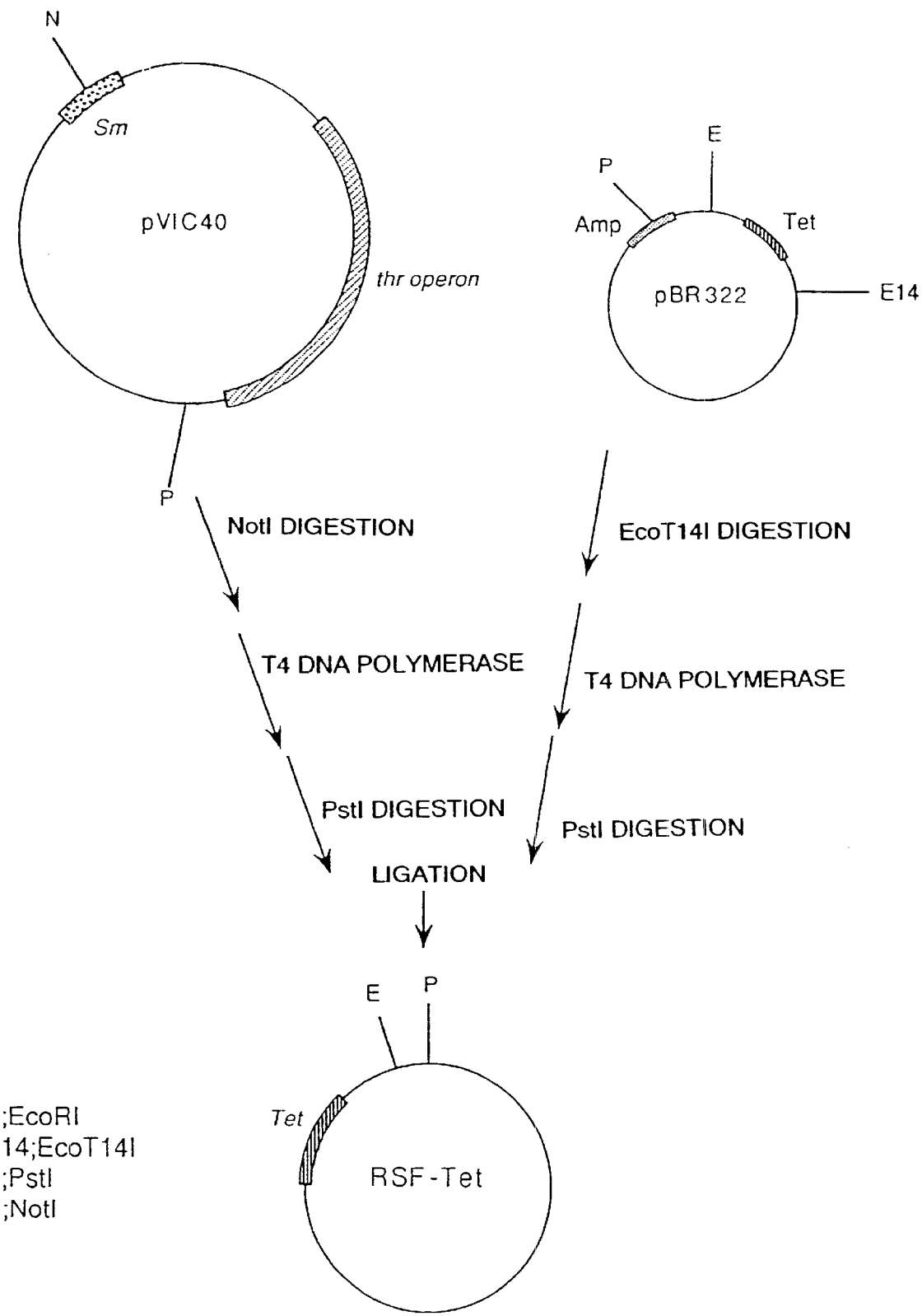
FIG. 7 shows construction of a plasmid RSF-Tet containing a replication origin of a broad-host-range plasmid RSF1010 and a tetracycline resistance gene.

The procedures of preparing a plasmid having the gltA gene, the ppc gene and the gdhA gene will be explained by referring to FIGS. 6 and 7.

A plasmid having the gdhA gene derived from *Escherichia coli*, pBRGDH (Japanese Patent Application Laid-open No. 7-203980), was digested with HindIII and SphI, the both ends were blunt-ended by the T4 DNA polymerase treatment, and then the DNA fragment having the gdhA gene was purified and recovered. Separately, a plasmid having the gltA gene and ppc gene derived from *Escherichia coli*, pMWCP (WO97/08294), was digested with XbaI, and then the both ends were blunt-ended by using T4 DNA polymerase. This was mixed with the above purified DNA fragment having the gdhA gene and ligated by using T4 ligase to obtain a plasmid pMWCPG, which corresponded to pMWCP further containing the gdhA gene (FIG. 6).

At the same time, the plasmid pVIC40 (Japanese Patent Application Laid-open No. 8-047397) having the replication origin of the broad-host-range plasmid RSF1010 was digested with NotI, treated with T4 DNA polymerase and digested with PstI. pBR322 was digested with EcoT14I, treated with T4 DNA polymerase and digested with PstI. The both products were mixed and ligated by using T4 ligase to obtain a plasmid RSF-Tet having the replication origin of RSF1010 and the tetracycline resistance gene (FIG. 7).

Figure 8:
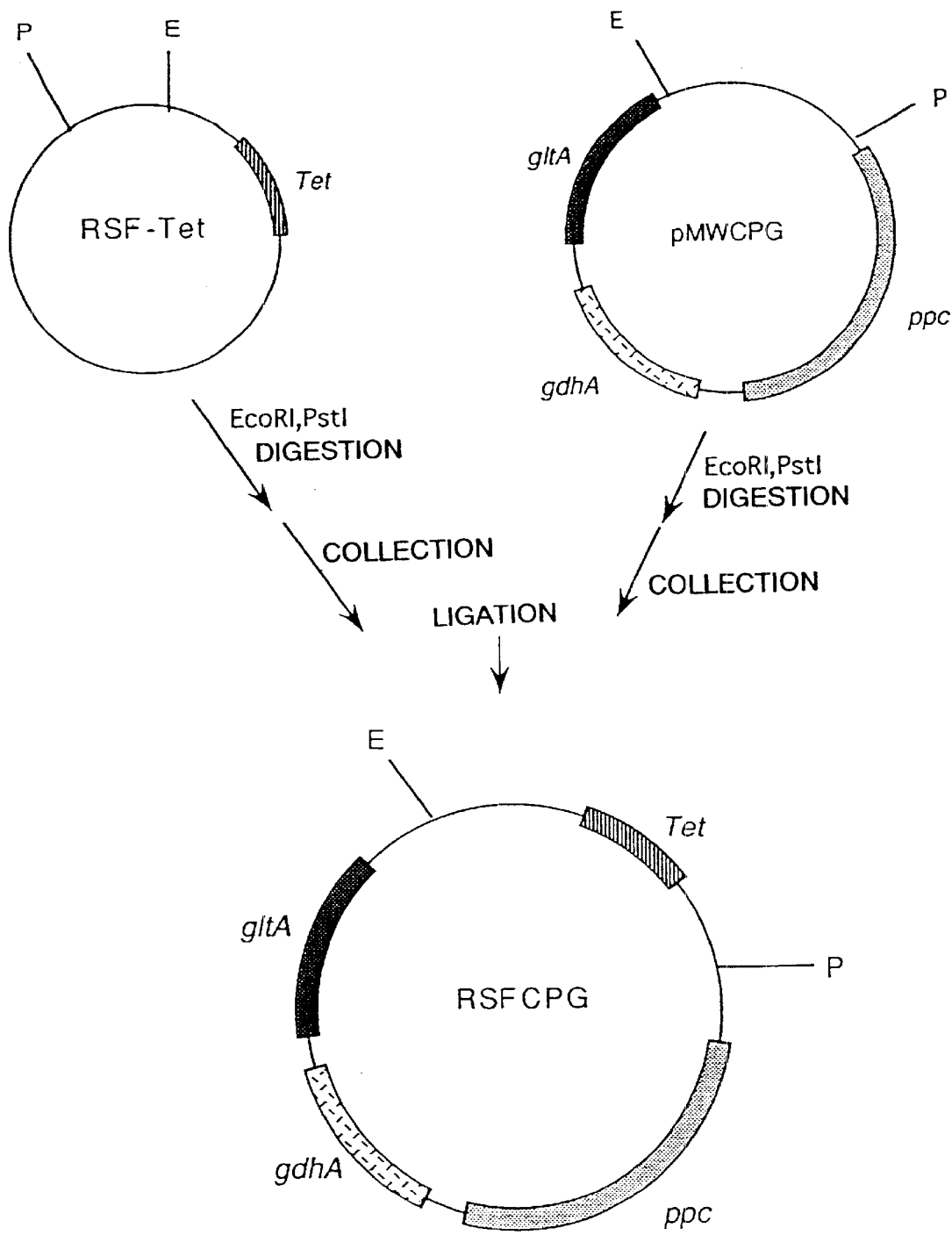
FIG. 8 shows construction of a plasmid RSFCPG containing a replication origin of a broad-host-range plasmid RSF1010, a tetracycline resistance gene, a gltA gene, a ppc gene and a gdhA gene.

Subsequently, pMWCPG was digested with EcoRI and PstI, and a DNA fragment having the gltA gene, the ppc gene and the gdhA gene was purified and recovered. RSF-Tet was similarly digested with EcoRI and PstI, and a DNA fragment having the replication origin of RSF1010 was purified and recovered. The both products were mixed and ligated by using T4 ligase to obtain a plasmid RSFCPG, which corresponded to RSF-Tet containing the gltA gene, the ppc gene and the gdhA gene (FIG. 8). It was confirmed that the obtained plasmid RSFCPG expressed the gltA gene, the ppc gene and the gdhA gene based on the supplementation of the auxotrophy of the gltA gene-, ppc gene- or gdhA gene-deficient strain derived from *Escherichia coli* and measurement of each enzyme activity.

(ii) Preparation of Plasmid Having gltA Gene Derived From *Brevibacterium Lactofermentum*

Figure 9:
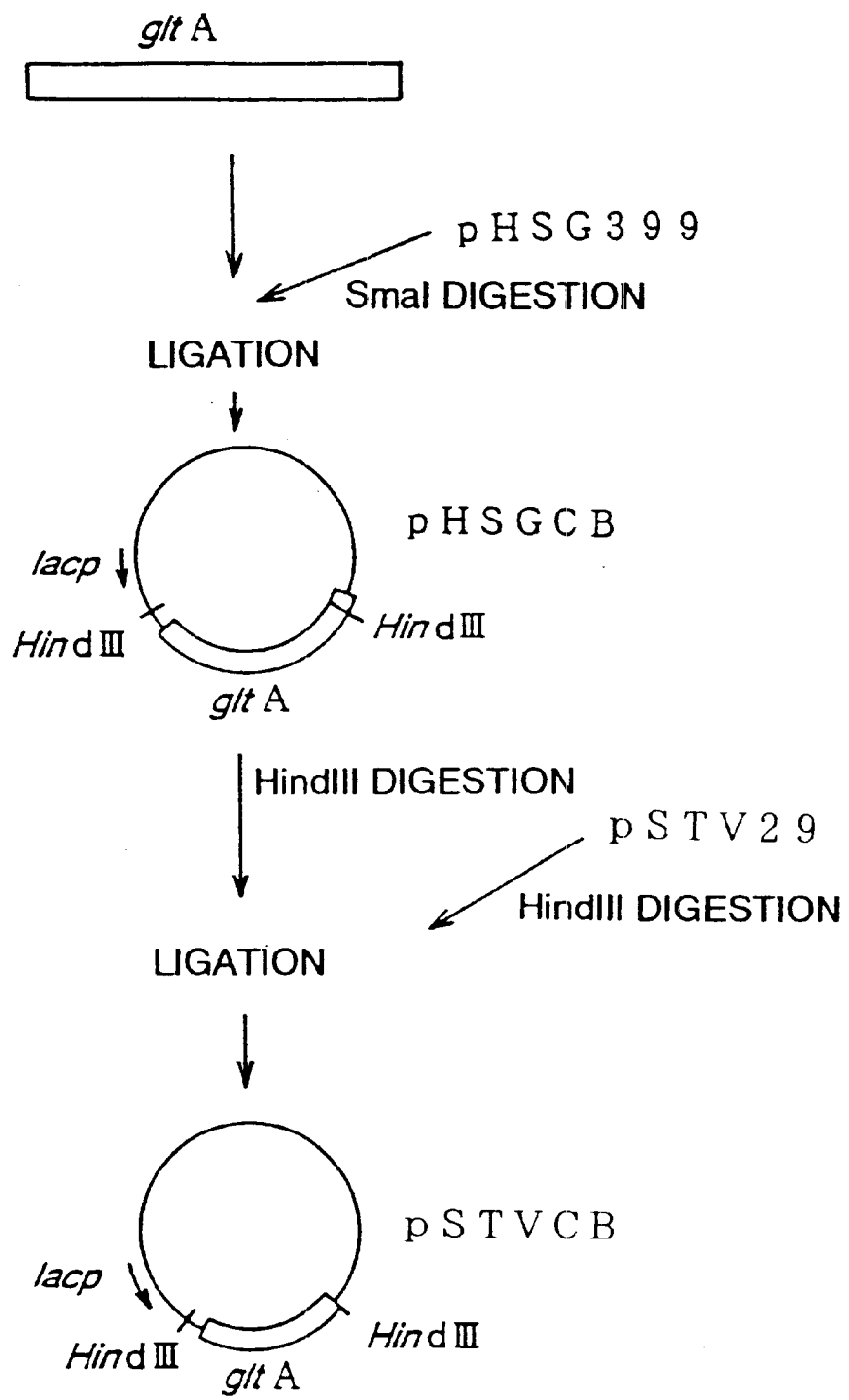
FIG. 9 shows the construction of plasmid pSTVCB containing a gltA gene.

A plasmid having the gltA gene derived from *Brevibacterium lactofermentum* was constructed as follows. PCR was performed by using the primer DNAs which were prepared based on the nucleotide sequence of the *Corynebacterium glutamicum* gltA gene (Microbiology, 140, pp.1817–1828 (1994)), and chromosomal DNA of *Brevibacterium lactofermentum* ATCC13869 as a template to obtain a gltA gene fragment of about 3 kb. This fragment was inserted into a plasmid pHSG399 (purchased from Takara Shuzo Co., Ltd.) digested with SmaI to obtain a plasmid pHSGCB (FIG. 9). Subsequently, pHSGCB was digested with HindIII, and the excised gltA gene fragment of about 3 kb was inserted into a plasmid pSTV29 (purchased from Takara Shuzo Co., Ltd.) digested with HindIII to obtain a plasmid pSTVCB (FIG. 9). It was confirmed that the obtained plasmid pSTVCB expressed the gltA gene by measuring the enzyme activity in the *Enterobacter agglomerans* AJ13355 strain.

(iii) Introduction of RSFCPG and pSTVCB into SC17sucA Strain

The *Enterobacter agglomerans* SC17sucA strain was transformed with RSFCPG by electroporation to obtain a transformant SC17sucA/RSFCPG strain showing tetracycline resistance. Further, the SC17sucA/RSFCPG strain was transformed with pSTVCB by electroporation to obtain a transformant SC17sucA/RSFCPG+pSTVCB strain showing chloramphenicol resistance.

<5> Acquisition of Strain with Improved Resistance to L-glutamic Acid in Low pH Environment A strain with improved resistance to L-glutamic acid at a high concentration in a low pH environment (hereafter, also referred to as "strain with high-concentration Glu-resistance at low pH") was isolated from the *Enterobacter agglomerans* SC17sucA/RSFCPG+pSTVCB strain.

The SC17sucA/RSFCPG+pSTVCB strain was cultured overnight at 30° C. in LBG medium (10 g/L of trypton, 5 g/L of yeast extract, 10 g/L of NaCl, 5 g/L of glucose), and the cells washed with saline was appropriately diluted and plated on an M9-E medium (4 g/L of glucose, 17 g/L of $Na_2HPO_4.12H_2O$, 3 g/L of $KH_2PO_4$, 0.5 g/L of NaCl, 1 g/L of $NH_4Cl$, 10 mM of $MgSO_4$, 10 μM of $CaCl_2$, 50 mg/L of L-lysine, 50 mg/L of L-methionine, 50 mg/L of DL-diaminopimelic acid, 25 mg/L of tetracycline, 25 mg/L of chloramphenicol, 30 g/L of L-glutamic acid, adjusted to pH 4.5 with aqueous ammonia) plate. A colony emerged after culture at 32° C. for 2 days was obtained as a strain with high-concentration Glu-resistance at low pH.

For the obtained strain, growth level in M9-E liquid medium was measured and L-glutamic acid-producing ability was tested in a 50-ml volume large test tube containing 5 ml of L-glutamic acid production test medium (40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride and 25 mg/L of chloramphenicol). A strain that exhibited the best growth level and the same L-glutamic acid-producing ability as that of its parent strain, the SC17/RSFCPG+pSTVCB strain, was designated as *Enterobacter agglomerans* AJ13601. The AJ13601 strain was deposited at the National Institute of Bioscience and Human-Technology, Agency of Industrial science and Technology, Ministry of International Trade and Industry (now, International Patent Organism Depositary, National Institute of Advanced Industrial Science and Technology; Central 6, Higashi 1-1-1, Tsukuba-shi, Ibaraki 305-8566, Japan) on Aug. 18, 1999 and received an accession number of FERM P-17516. It was then transferred to an international deposition under the provisions of Budapest Treaty on Jul. 6, 2000 and received an accession number of FERM BP-7207.

Example 1

Growth Inhibition by Organic Acid at Acidic pH

Although the *Enterobacter agglomerans* AJ13601 strain can grow in a wide pH range from neutral pH to acidic pH, the inhibition of growth by an organic acid is particularly remarkable at an acidic pH. Therefore, an experiment concerning the growth inhibition by an organic acid was performed at an acidic pH.

The *Enterobacter agglomerans* AJ13601 strain was cultured on LBG agar medium (10 g/L of trypton, 5 g/L of yeast extract, 10 g/L of NaCl and 15 g/L of agar) containing 25 mg/L of tetracycline hydrochloride and 25 mg/L of chloramphenicol at 30° C. for 14 hours, and one platinum loop of the cells were taken and inoculated into 300 mL of a seed culture medium having the following composition in a 1 L-volume jar fermenter to perform seed culture at 34° C. at pH 6.0.

[Composition of Seed Culture Medium]

50 g/L of sucrose, 0.4 g/L of magnesium sulfate heptahydrate, 4.0 g/L of ammonium sulfate, 2.0 g/L of monopotassium dihydrogenphosphate, 4.0 g/L of yeast extract, 0.01 g/L of ferrous sulfate heptahydrate, 0.01 g/L manganese sulfate pentahydrate, 0.4 g/L of L-lysine hydrochloride, 0.4 g/L of DL-methionine, 0.4 g/L of DL-α, ε-diaminopimelic acid, 25 mg/L of tetracycline hydrochloride and 25 mg/L of chloramphenicol pH was controlled by adding ammonia gas during the culture. The seed culture was terminated by observing depletion of the saccharide in the seed culture medium as a marker, and the seed culture broth was inoculated into 300 mL of a main culture medium contained in 1 L-volume jar fermenters in an amount of 20% of the volume of the main culture medium to perform the main culture. The composition of the main culture medium is shown below. When an experiment for the growth inhibition by an organic acid is performed, the experiment was performed by adding the organic acid at a predetermined concentration.

[Composition of Main Culture Medium]

20 g/L of glucose, 0.4 g/L of magnesium sulfate heptahydrate, 5.0 g/L of ammonium sulfate, 6.0 g/L of monopotassium dihydrogenphosphate, 1.5 g/L of sodium chloride, 0.01 g/L of ferrous sulfate heptahydrate, 0.01 g/L of manganese sulfate pentahydrate, 0.8 g/L of L-lysine hydrochloride, 0.6 g/L of DL-methionine, 0.6 g/L of DL-α, ε-diaminopimelic acid, 25 mg/L of tetracycline hydrochloride, 25 mg/L of chloramphenicol, 6.0 g/L of yeast extract and 0.75 g/L of calcium chloride dihydrate The culture temperature was adjusted to 34° C., and pH was controlled to a predetermined pH by adding ammonia gas.

Figure 10:
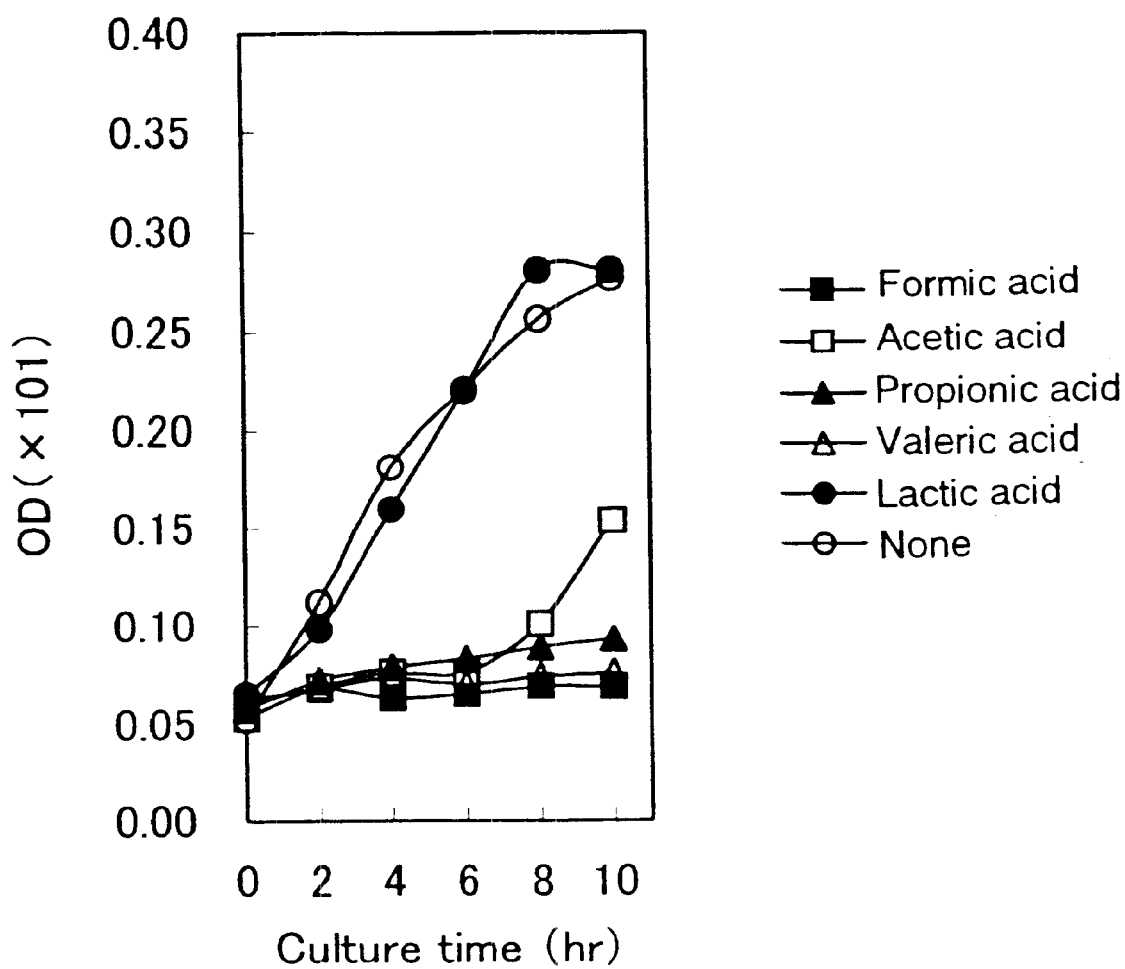
FIG. 10 shows growth inhibition effect of various organic acids at an acidic pH (pH 4.5).

Experiments for the growth inhibition effect at an acidic pH (pH 4.5) were first performed with various organic acids. The experiments were performed by adding each of formic acid, acetic acid, lactic acid, propionic acid, valeric acid, succinic acid, fumaric acid, malic acid, oxalacetic acid and citric acid at a concentration of 0.5 g/L to the main culture medium. A part of the results of these experiments are shown in FIG. 10.

As shown by these results, formic acid, acetic acid and propionic acid showed evident growth inhibition. On the other hand, lactic acid allowed a growth rate comparable to that obtained with the control medium not supplemented with an organic acid (besides that, succinic acid, fumaric acid and malic acid did not show growth inhibition, either). There is also a report that the microbial growth inhibition by an organic acid at an acidic pH is caused because the organic acid that lost charge under an acidic pH condition passes through a cytoplasmic membrane and is dissociated again under a neutral pH condition in a cell, and this conception is explained by using a dissociation constant pKa of an organic acid.

TABLE 1

| Organic acid | pKa | Growth inhibition |
| --- | --- | --- |
| Formic acid | 3.75 | Observed |
| Lactic acid | 3.86 | Not observed |
| Succinic acid | 4.21 | Not observed |
| Acetic acid | 4.76 | Observed |
| Propionic acid | 4.87 | Observed |

However, the results of the above experiments cannot be explained based on pKa, and the growth inhibition of the *Enterobacter agglomerans* AJ13601 strain by formic acid, acetate and propionic acid is considered to be caused by another inhibition mechanism, which cannot be explained by the conception of the previous report.

Figure 11:
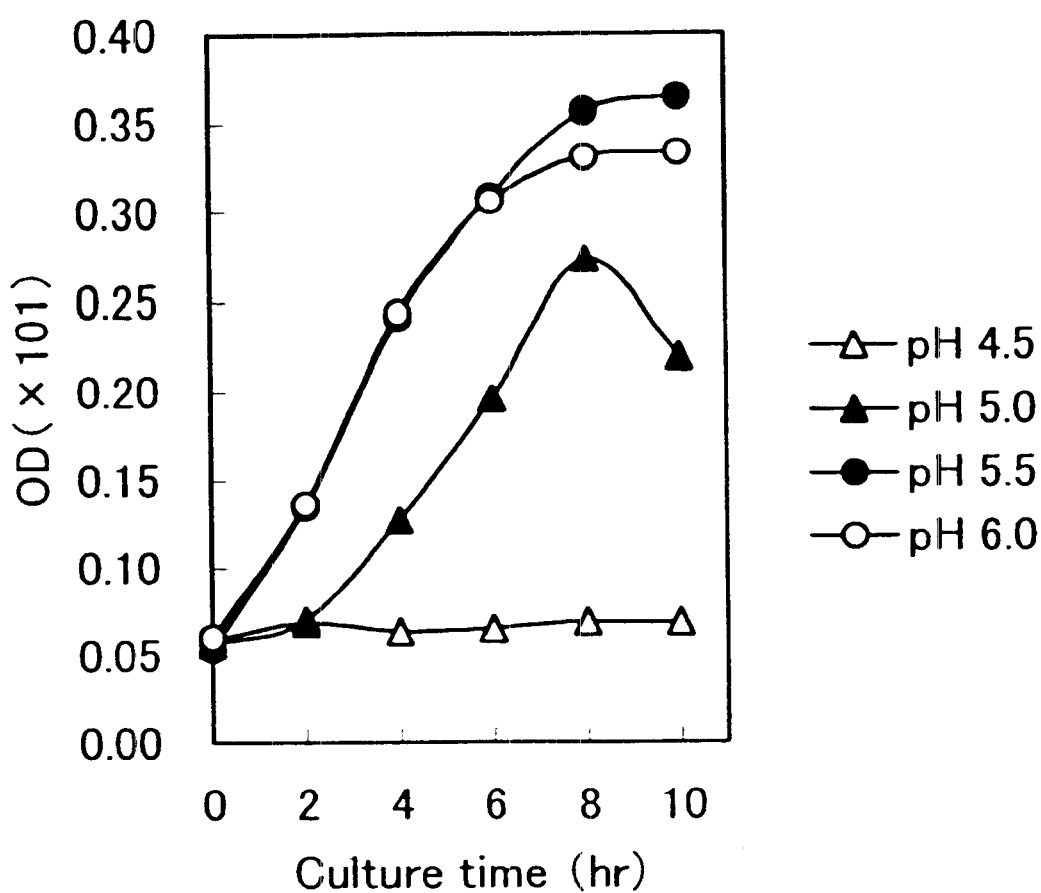
FIG. 11 shows results of investigation using formic acid for pH at which growth inhibition is caused.

Then, pH causing growth inhibition was investigated by using formic acid (concentration: 0.5 g/L). The results are shown in FIG. 11. It became clear that the growth inhibition by formic acid was not observed in a pH region of 5.5 or more, but was observed at a pH lower than that. In particular, at pH 4.5, growth of cells was hardly observed.

Figure 12:
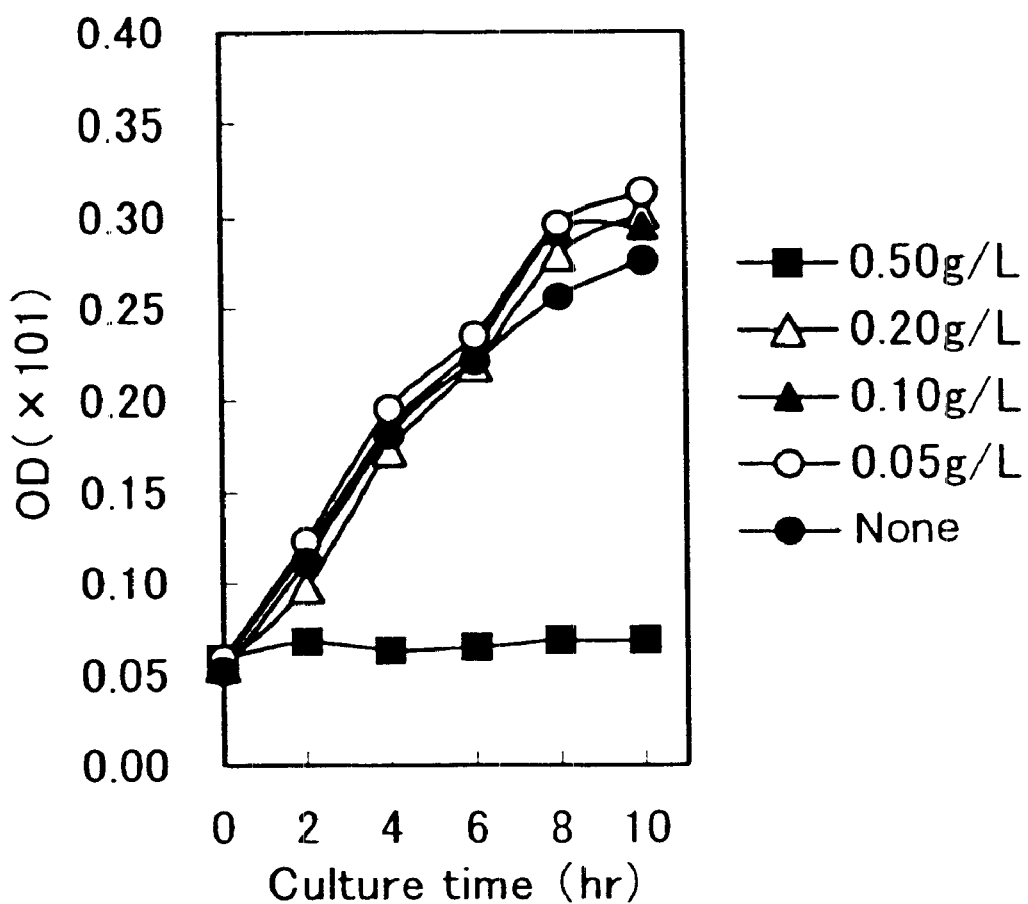
FIG. 12 shows results of investigation for formic arid concentration that causes growth inhibition under a condition of pH 4.5.

Further, formic acid concentration causing growth inhibition under a condition of pH 4.5 was also investigated. The results are shown in FIG. 12. From the results, it became clear that the growth inhibition was not observed when the formic acid concentration in the medium was 0.20 g/L or less, but the growth inhibition was observed at a concentration higher than a certain level within the range of 0.2 to 0.5 g/L.

Based on the above experimental results, it is concluded that, in order to enable culture of the *Enterobacter agglomerans* AJ13601 strain at an acidic pH utilizing a carbon source (saccharide) containing an organic acid such as beet molasses and cane molasses and a nitrogen source such as corn steep liquor (CSL), soybean protein hydrolysis solution, animal protein hydrolysis solution (meat extract) and casein hydrolysate, it is necessary to lower a concentration of an organic acid showing the inhibition such as formic acid and acetic acid in a medium, or in order to produce L-glutamic acid at an acidic pH, there is required a culture method comprising culturing cells in a pH range where the growth inhibition is not observed so that the organic acid showing the inhibition should be consumed and then culturing the cells at a shifted acidic pH, as in Example 2 mentioned below.

Example 2

Reduction of Growth Inhibition by Organic Acid Through Culture with pH Shift Cell growth of the *Enterobacter agglomerans* AJ13601 strain is inhibited by a low molecular organic acid such as formic acid at an acidic pH as demonstrated in Example 1. Therefore, because many of such natural raw materials, including beet molasses and cane molasses, contain marked amounts of such organic acids, the *Enterobacter agglomerans* AJ13601 strain cannot be cultured at an acidic pH using the natural raw materials. However, because the growth inhibition by organic acids was observed only at an acidic pH, but not observed at a neutral pH, it was attempted to produce glutamic acid by performing the culture at a neutral pH for an early stage of the culture to consume organic acids causing the growth inhibition and then shifting pH to an acidic pH to produce glutamic acid.

The *Enterobacter agglomerans* AJ13601 strain was cultured on LBG agar medium (10 g/L of trypton, 5 g/L of yeast extract, 10 g/L of NaCl and 15 g/L of agar) containing 25 mg/L of tetracycline hydrochloride and 25 mg/L of chloramphenicol at 30° C. for 14 hours, and one platinum loop of the cells were taken and inoculated into 300 mL of a seed culture medium having the following composition in a 1 L-volume jar fermenter to perform seed culture at 34° C. at pH 6.0.
[Composition of Seed Culture Medium]

50 g/L of sucrose, 0.4 g/L of magnesium sulfate heptahydrate, 4.0 g/L of ammonium sulfate, 2.0 g/L of monopotassium dihydrogenphosphate, 4.0 g/L of yeast extract, 0.01 g/L of ferrous sulfate heptahydrate, 0.01 g/L manganese sulfate pentahydrate, 0.4 g/L of L-lysine hydrochloride, 0.4 g/L of DL-methionine, 0.4 g/L of DL-α, ε-diaminopimelic acid, 25 mg/L of tetracycline hydrochloride and 25 mg/L of chloramphenicol pH was controlled by adding ammonia gas during the culture. The seed culture was terminated by observing depletion of the saccharide in the seed culture medium as a marker, and the seed culture broth was inoculated into 300 mL of a main culture medium contained in a 1 L-volume jar fermenter in an amount of 20% of the volume of the main culture medium to perform the main culture. The composition of the main culture medium is shown below.
[Composition of Main Culture Medium]

20 g/L of beet molasses (or cane molasses), 0.4 g/L of magnesium sulfate heptahydrate, 5.0 g/L of ammonium sulfate, 6.0 g/L of monopotassium dihydrogenphosphate, 1.5 g/L of sodium chloride, 0.01 g/L of ferrous sulfate heptahydrate, 0.01 g/L of manganese sulfate pentahydrate, 0.8 g/L of L-lysine hydrochloride, 0.6 g/L of DL-methionine, 0.6 g/L of DL-α,ε-diaminopimelic acid, 25 mg/L of tetracycline hydrochloride, 25 mg/L of chloramphenicol, 6.0 g/L of yeast extract and 0.75 g/L of calcium chloride dihydrate The culture temperature was adjusted to 34° C., and pH was controlled to a predetermined pH by adding ammonia gas. The culture was started at pH 6.0 and performed until the saccharide and organic acid in the main culture medium were consumed. After the saccharide was depleted, 700 g/L of an aqueous solution of glucose was continuously added (5 ml/hr). While glucose was continuously added, the addition amount of ammonia gas was controlled and pH reduction in connection with the glutamic acid production was utilized to lower pH to a level of 4.5 over about 2 hours, and then the culture was continued at pH 4.5. When the glutamic acid concentration in the culture broth reached 45 g/L, 1.0 g of glutamic acid crystals were added to the main culture medium as seed crystals to promote precipitation of crystals in the culture broth.

As a result of the culture for 50 hours, a marked amount of glutamic acid crystals were precipitated in the jar fermenter. Then, ammonia gas was added so as to increase pH to 6.0 to dissolve the whole glutamic acid crystals in the jar fermenter, and then the amount of the produced glutamic acid was measured. Further, culture was performed in the same manner as above except that pH was maintained to be 4.5 from an early stage of the culture, and amount of the produced glutamic acid was measured. In this case, because cells were decreased, the culture was terminated in 28 hours. The results are shown in Table 2.

TABLE 2

Comparison of fermentation results

| Culture method | OD (x101) | Amount of produced glutamic acid (g) |
|---|---|---|
| With pH shift | 0.753 | 50.4 |
| With constant pH (4.5) | 0.078 | 2.6 |

Figure 13:
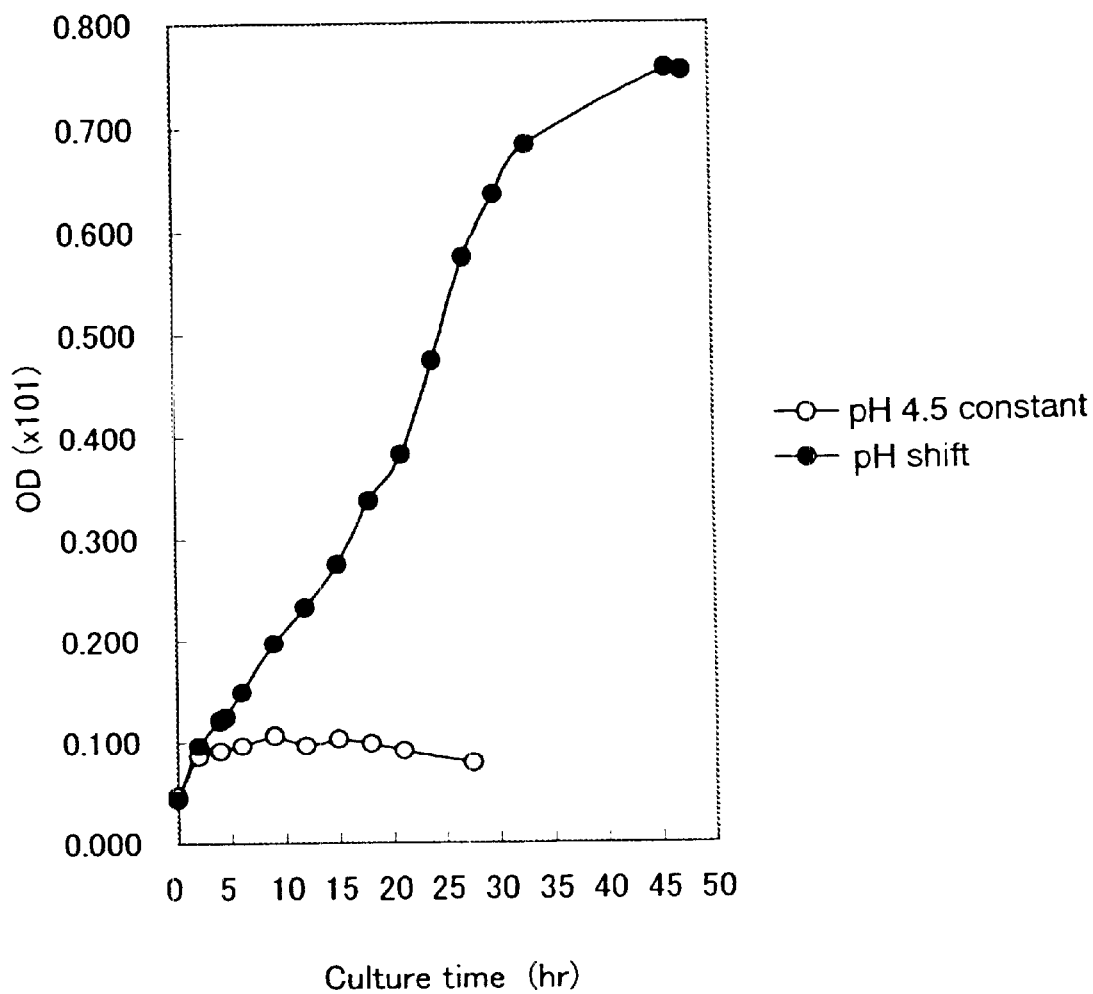
FIG. 13 shows a time course of cell growth during culture.

Further, a time course of growth of the cells was measured based on optical density (OD) at a wavelength of 620 nm. The results are shown in FIG. 13.

As a result, it was found that, in the experiment where the culture was performed at an acidic pH from an early stage of culture, cell growth was inhibited and thus L-glutamic acid production was hardly observed, whereas, in the experiment where culture was performed by using pH shift, crystals of glutamic acid precipitated in the culture broth, and thus it was demonstrated that natural raw materials containing an organic acid could be used in the method.

From the results mentioned above, it was confirmed that the culture using pH shift enabled culture with precipitation of crystals of glutamic acid at an acid pH even by using natural raw materials containing organic acids.

What is claimed is:

1. A method for producing L-glutamic acid by fermentation, which comprises culturing a microorganism having L-glutamic acid producing ability in a medium having a pH of 5.0 or less, wherein the medium contains an organic acid having 1, 2, or 3 carbon atoms, wherein the amount of the organic acid in the medium is 0.4 g/L or less, and wherein the amount of the organic acid in the medium does not inhibit the growth of the microorganism.

2. The method according to claim 1, wherein L-glutamic acid is produced and accumulated in the medium, and wherein the L-glutamic acid precipitates during the culture in the medium.

3. The method according to claim 1 or 2, wherein the microorganism belongs to the genus Enterobacter.

4. The method according to claim 3, wherein the microorganism is *Enterobacter agglomerans*.

5. The method according to claim 1 or 2, wherein the microorganism can metabolize a carbon source in a liquid medium containing L-glutamic acid at a saturation concentration and the carbon source, at a specific pH, and has an ability to accumulate L-glutamic acid in an amount exceeding the saturation concentration of L-glutamic acid in the liquid medium at the pH.

6. The method according to claim 5, wherein the specific pH is 5.0 or less.

7. A method for producing L-glutamic acid by fermentation, which comprises culturing in a medium comprising an organic acid having 1, 2, or 3 carbon atoms a microorganism having L-glutamic acid-producing ability at a first pH at which growth of the microorganism is not inhibited by the organic acid in the medium, and then culturing the microorganism at a second pH that is suitable for L-glutamic acid production by the microorganism and is lower than the first pH,
wherein the culture at the first pH is performed while pH of the medium is maintained to be the first pH by adding an alkalizing substance to the medium.

8. The method according to claim 1, wherein the second pH is 3.0 to 5.0.

9. The method according to claim 7, which comprising lowering pH of the medium by controlling the addition amount of the alkalizing substance after the culture at the first pH.

10. The method according to claim 7, wherein the culture at the first pH is continued until the organic acid in the medium is depleted.

11. The method according to claim 7, wherein the microorganism belongs to the genus Enterobacter.

12. The method according to claim 11, wherein the microorganism is *Enterobacter agglomerans*.

13. The method according to claim 7, wherein the microorganism can metabolize a carbon source in a liquid medium containing L-glutamic acid at a saturation concentration and the carbon source, at a specific pH, and has an ability to accumulate L-glutamic acid in an amount exceeding the saturation concentration of L-glutamic acid in the liquid medium at the pH.

14. The method according to claim 13, wherein the specific pH is 5.0 or less.

15. The method according to claim 13 or 14, wherein the pH suitable for the L-glutamic acid production is a pH at which L-glutamic acid produced by the microorganism precipitates in the medium, and L-glutamic acid is produced and accumulated with precipitation of the L-glutamic acid accompanied, during the culture in the medium at the pH.

* * * * *

UNITED STATES PATENT AND TRADEMARK OFFICE
CERTIFICATE OF CORRECTION

PATENT NO.   : 6,653,110 B2
DATED        : November 25, 2003
INVENTOR(S)  : Masakazu Sato et al.

It is certified that error appears in the above-identified patent and that said Letters Patent is hereby corrected as shown below:

Column 38,
Line 50, "according to claim 1," should read -- according to claim 7, --.

Signed and Sealed this

First Day of June, 2004

JON W. DUDAS
*Acting Director of the United States Patent and Trademark Office*